United States Patent
Linker et al.

(10) Patent No.: US 6,420,316 B1
(45) Date of Patent: *Jul. 16, 2002

(54) SUBSTITUTED AROMATIC THIOCARBOXYLIC ACID AMIDES AND THEIR USE AS HERBICIDES

(75) Inventors: Karl-Heinz Linker; Kurt Findeisen, both of Leverkusen; Roland Andree; Mark-Wilhelm Drewes, both of Langenfeld; Andreas Lender, Wuppertal; Otto Schallner, Monheim; Wilhelm Haas, Pulheim; Hans-Joachim Santel; Markus Dollinger, both of Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/945,855

(22) Filed: Sep. 4, 2001

Related U.S. Application Data

(62) Division of application No. 09/470,583, filed on Dec. 22, 1999, now Pat. No. 6,331,507, which is a division of application No. 08/732,257, filed as application No. PCT/EP95/01507 on Apr. 21, 1995, now Pat. No. 6,077,813.

(30) Foreign Application Priority Data

May 4, 1994 (DE) ............................................. 44 15 655
Jan. 10, 1995 (DE) ......................................... 195 00 439

(51) Int. Cl.[7] ...................... A01N 43/653; C07D 249/08
(52) U.S. Cl. ................................... 504/273; 548/263.8
(58) Field of Search ........................ 504/273; 548/263.8

(56) References Cited

U.S. PATENT DOCUMENTS

| | | | |
|---|---|---|---|
| 3,338,913 A | 8/1967 | Yates et al. | 260/294.8 |
| 4,112,095 A | 9/1978 | Allen, Jr, et al. | 424/250 |
| 4,503,054 A | 3/1985 | Brown et al. | 504/272 |
| 4,515,791 A | 5/1985 | Allen, Jr. et al. | 514/248 |
| 4,734,415 A | 3/1988 | Sircar et al. | 514/247 |
| 5,006,148 A | 4/1991 | Fischer et al. | 71/72 |
| 5,124,342 A | 6/1992 | Kedersky et al. | 514/514 |
| 5,204,352 A | 4/1993 | Sundberg et al. | 514/258 |
| 5,639,770 A | 6/1997 | Chihiro et al. | 514/365 |
| 6,077,813 A | * 6/2000 | Linker et al. | 504/272 |

FOREIGN PATENT DOCUMENTS

| | | |
|---|---|---|
| DE | 21 62 439 | 6/1973 |
| DE | 22 04 767 | 8/1973 |
| EP | 0 052 442 | 5/1982 |
| EP | 0 370 332 | 5/1990 |
| EP | 0 384 362 | 8/1990 |
| EP | 0537 980 | 4/1993 |
| EP | 0 542 363 | 5/1993 |
| GB | 1 080 246 | 8/1967 |
| GB | 1 215 858 | 12/1970 |
| JP | 02193994 | 7/1990 |
| WO | WO 90/09381 | 8/1990 |
| WO | WO 93/14077 | 7/1993 |
| WO | WO 93/22303 | 11/1993 |
| WO | W 93/24472O | 12/1993 |

OTHER PUBLICATIONS

CA 114:6530s (Abstract) 1991, p. 646.
J. Hetero.Chem., vol. 25, No. 1, 1998, pp. 129–137, Sundberg et al., "Preparation of 2–arly . . . compounds".
J. Med.Chem., vol. 30, No. 6, 1987, pp. 1023–1029, Sicar et al., "Cardiotonic agents . . . intropic activity".
CA 103:71307m (Abstract) 1985, p. 652.
CA 91:184919q (Abstract) 1979, pp. 646–647.
Sircar et al. (Cardiotonic Agents., J. Med.Chem., 30(11) 1987, pp. 1955–1962.

* cited by examiner

*Primary Examiner*—Richard L. Raymond
(74) *Attorney, Agent, or Firm*—Norris McLaughlin & Marcus

(57) ABSTRACT

Disclosed are substituted aromatic thiocarboxamide compounds of the formula:

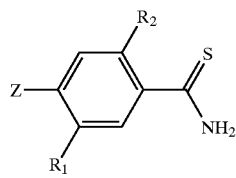

their use as herbicides and the process of making said compounds.

10 Claims, No Drawings

SUBSTITUTED AROMATIC THIOCARBOXYLIC ACID AMIDES AND THEIR USE AS HERBICIDES

This application is a divisional of application Ser. No. 09/470,583, filed on Dec. 22, 1999 now U.S. Pat. No. 6,331,507, which is a divisional of application Ser. No. 08/732,257, filed on Oct. 28, 1996, now U.S. Pat. No. 6,077,813, issued Jun. 20, 2000, which is a 371 of PCT/EP 95/01507, filed Apr. 21, 1995.

The invention relates to novel substituted aromatic thiocarboxamides, to processes for their preparation and to their use as herbicides.

It is already known that certain aromatic carbothioamides, for example 2,6-dichloro-benzothioamide ("chlorthiamid"), possess herbicidal properties (cf. GB-B 987253). However, the activity of this previously known compound, especially at low application rates and concentrations, is not entirely satisfactory in all areas of application.

The novel substituted aromatic thiocarboxamides have now been found of the general formula (I)

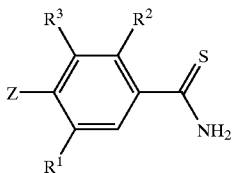

(I)

in which
R$^1$ represents hydrogen or halogen,
R$^2$ represents the following group

—A$^1$—A$^2$—A$^3$ in which
A$^1$ represents a single bond, or represents oxygen, sulphur, —SO—, —SO$_2$—, —CO— or the group —N—A$^4$—, in which A$^4$ represents hydrogen, hydroxyl, alkyl, alkenyl, alkinyl, alkoxy, aryl, alkylsulphonyl or arylsulphonyl,
A$^1$ additionally represents in each case optionally substituted alkanediyl, alkenediyl, alkinediyl, cycloalkanediyl, cycloalkenediyl or arenediyl,
A$^2$ represents a single bond, or represents oxygen, sulphur, —SO—, —SO$_2$—, —CO— or the group —N—A$^4$—, in which A$^4$ represents hydrogen, hydroxyl, alkyl, alkenyl, alkinyl, aryl, alkoxy, alkylsulphonyl or arylsulphonyl,
A$^2$ additionally represents in each case optionally substituted alkanediyl, alkenediyl, alkinediyl, cycloalkanediyl, cycloalkenediyl or arenediyl,
A$^3$ represents hydrogen, hydroxyl, amino, cyano, isocyano, thiocyanato, nitro, carboxyl, carbamoyl, thiocarbamoyl, sulpho, chlorosulphonyl, halogen or represents in each case optionally substituted alkyl, alkoxy, alkylthio, alkylsulphinyl, alkylsulphonyl, alkylamino, dialkylamino, alkoxycarbonyl, dialkoxy(thio)phosphoryl, alkenyl, alkenyloxy, alkenylamino, alkylideneamino, alkenyloxycarbonyl, alkinyl, alkinyloxy, alkinylamino, alkinyloxycarbonyl, cycloalkyl, cycloalkyloxy, cycloalkylalkyl, cycloalkylalkoxy, cycloalkylideneamino, cycloalkyloxycarbonyl, cycloalkylalkoxycarbonyl, aryl, aryloxy, arylalkyl, arylalkoxy, aryloxycarbonyl, arylalkoxycarbonyl, heterocyclyl, heterocyclylalkyl, heterocyclylalkoxy or heterocyclylalkoxycarbonyl,
R$^3$ represents hydrogen or halogen or together with R$^2$ represents an alkanediyl or an alkenediyl group which optionally contains at the beginning (or end) or within the hydrocarbon chain an oxygen atom, a sulphur atom, an SO$_2$ group, an NH group, an N-alkyl group, a carbonyl group and/or a thiocarbonyl group, and
Z represents in each case optionally substituted monocyclic or bicyclic, saturated or unsaturated heterocyclyl, heterocyclylamino or heterocyclylimino.

The novel substituted aromatic thiocarboxamides of the general formula (I) are obtained if substituted aromatic nitriles of the general formula (II)

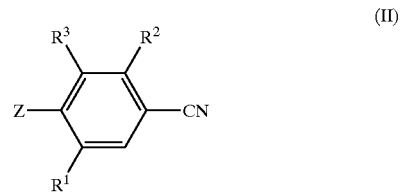

(II)

in which
R$^1$, R$^2$, R$^3$ and Z have the meanings given above are reacted with hydrogen sulphide (H$_2$S) or with thioacetamide, optionally in the presence of a reaction auxiliary and optionally in the presence of a diluent.

The novel substituted aromatic thiocarboxamides of the general formula (I) are notable for strong and selective herbicidal activity.

In the definitions, the saturated or unsaturated hydrocarbon chains, such as alkyl, alkanediyl, alkenyl or alkinyl—alone or in conjunction with heteroatoms, such as in alkoxy, alkylthio or alkylamino—are each straight-chain or branched.

Halogen generally represents fluorine, chlorine, bromine or iodine, preferably fluorine, chlorine or bromine, especially fluorine or chlorine.

The invention preferably relates to compounds of the formula (I) in which
R$^1$ represents hydrogen, fluorine, chlorine or bromine,
R$^2$ represents the following group

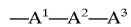
—A$^1$—A$^2$—A$^3$ in which
A$^1$ represents a single bond, or represents oxygen, sulphur, —SO—, —SO$_2$—, —CO— or the group —N—A$^4$—, in which A$^4$ represents hydrogen, hydroxyl, C$_1$–C$_4$-alkyl, C$_3$–C$_4$-alkenyl, C$_3$–C$_4$-alkinyl, C$_1$–C$_4$-alkoxy, phenyl, C$_3$–C$_4$-alkylsulphonyl or phenylsulphonyl,
A$^1$ additionally represents in each case optionally fluorine- or chlorine-substituted C$_1$–C$_6$-alkanediyl, C$_2$–C$_6$-alkenediyl, C$_2$–C$_6$-alkinediyl, C$_3$–C$_6$-cycloalkanediyl, C$_3$–C$_6$-cycloalkenediyl or phenylene,
A$^2$ represents a single bond, or represents oxygen, sulphur, —SO—, —SO$_2$—, —CO— or the group —N—A$^4$—, in which A$^4$ represents hydrogen, hydroxyl, C$_1$–C$_4$-alkyl, C$_3$–C$_4$-alkenyl, C$_3$–C$_4$-alkinyl, C$_1$–C$_4$-alkoxy, phenyl, C$_1$–C$_4$-alkylsulphonyl or phenylsulphonyl, A² additionally represents in each case optionally fluorine- or chlorine-substituted $C_1$–$C_6$-alkanediyl, $C_2$–$C_6$-alkenediyl, $C_2$–$C_6$-alkinediyl, $C_3$–$C_6$-cycloalkanediyl, $C_3$–$C_6$-cycloalkenediyl or phenylene, A³ represents hydrogen, hydroxyl, amino, cyano, isocyano, thiocyanato, nitro, carboxyl, carbamoyl, thiocarbamoyl, sulpho, chlorosulphonyl, halogen, or represents in each case optionally halogen- or $C_1$–$C_4$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups, or represents in each case optionally halogen-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, or represents in each case optionally halogen-, cyano-, carboxyl-, $C_1$–$C_4$-alkyl- and/or $C_1$–$C_4$-alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups, or represents in each case optionally nitro-, cyano-, carboxyl-, halogen-, $C_1$–$C_4$-alkyl-, $C_1$–$C_4$-halogenoalkyl-, $C_1$–$C_4$-alkyloxy-, $C_1$–$C_4$-halogenoalkyloxy- and/or $C_1$–$C_4$-alkoxy-carbonyl-substituted phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, (in each case optionally totally or partially hydrogenated) pyrrolyl, pyrazolyl, iridazolyl, triazolyl, fliryl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazole-$C_1$–$C_4$-alkyl, thiazole-$C_1$–$C_4$-alkyl, pyridinyl-$C_1$–$C_4$-alkyl, pyrimidinyl-$C_1$–$C_4$-alkyl, pyrazolylmethoxy or furylmethoxy, or represents perhydropyranylmethoxy or pyridylmethoxy, R³ represents hydrogen, fluorine, chlorine or bromine or together with R² represents an alkanediyl or alkenediyl group having in each case up to 4 carbon atoms which optionally contains at the beginning (or end) or within the hydrocarbon chain an oxygen atom, a sulphur atom, an $SO_2$ group, an NH group, an N—$C_1$–$C_4$-alkyl group, a carbonyl group and/or a thiocarbonyl group, and Z represents in each case monocyclic or bicyclic, saturated or unsaturated hetero-cyclyl, heterocyclylamino or heterocyclylimino having in each case 2 to 6 carbon atoms and 1 to 4 nitrogen atoms in the heterocyclic ring system, which optionally additionally contains an oxygen atom or sulphur atom and/or optionally up to three groups from the series —CO—, —CS—, —SO— and/or $SO_2$—, and which is optionally substituted by one or more groups from the series nitro, hydroxyl, amino, cyano, carboxyl, carbainoyl, thiocarbamoyl, halogen, $C_1$–$C_6$-alkyl (which is optionally substituted by halogen or $C_1$–$C_4$-alkoxy), $C_2$–$C_6$-alkenyl or $C_2$–$C_6$-alkinyl (which are in each case optionally substituted by halogen), $C_1$–$C_6$-alkoxy or $C_1$–$C_6$-alkoxy-carbonyl (which are in each case optionally substituted by halogen or $C_1$–$C_4$-alkoxy), $C_2$–$C_6$-alkenyloxy or $C_2$–$C_6$-alkinyloxy (which are in each case optionally substituted by halogen), $C_1$–$C_6$-alkylthio, $C_2$–$C_6$-alkenylthio or $C_2$–$C_6$-alkinylthio (which are in each case optionally substituted by halogen), $C_1$–$C_6$-alkylamino or di-($C_1$–$C_4$-alkyl)-amino, $C_3$–$C_6$-cycloalkyl or $C_3$–$C_6$-cycloalkyl-$C_1$–$C_4$-alkyl (which are in each case optionally substituted by halogen and/or $C_1$–$C_4$-alkyl), phenyl, phenoxy, phenylthio, phenylsulphinyl, phenylsulphonyl or phenylamino (which are in each case optionally substituted by nitro, cyano, halogen, $C_1$–$C_4$-alkyl, $C_1$–$C_4$-halogenoalkyl, $C_1$–$C_4$-alkyloxy, $C_1$–$C_4$-halogenoalkyloxy and/or $C_1$–$C_4$-alkoxy-carbonyl).

The invention particularly relates to compounds of the fonnula (I) in which

R¹ represents hydrogen, fluorine or chlorine,

R² represents the following group

—A¹—A²—A³ which

A¹ represents a single bond, or represents oxygen, sulphur, —SO—, —$SO_2$—, —CO— or the group —N—A⁴—, in which A⁴ represents hydrogen, hydroxyl, methyl, ethyl, n- or i-propyl, methoxy, ethoxy, n- or i-propoxy, methylsulphonyl or ethylsulphonyl, A² additionally represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, A² represents a single bond, or represents oxygen, sulphur, —SO—, —$SO_2$—, —CO— or the group —N—A⁴—, in which A⁴ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, A² additionally represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, A³ represents hydrogen, hydroxyl, amino, cyano, nitro, carboxyl, carbamoyl, sulpho, fluorine, chlorine, bromine, or represents in each case optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethyl;-thio, n- or i-propylthio, n-, i-, s- or t-butylthio, methylsulphinyl, ethyl-sulphinyl, n- or i-propylsulphinyl, methylsulphonyl, ethylsulphonyl, n- or i-propylsulphonyl, methylamino, ethylamino, n- or i-propylamino, n-, i-, s-or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, or represents in each case optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, or represents in each case optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl, cyclohexyl, cyclopropyl-oxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyciopentylmethoxycarbonyl or cyclohexyl-methoxycarbonyl, or represents in each case optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl, (in each case optionally completely or partially hydrogenated) pyrrolyl, pyrazolyl, imidazolyl, triazolyl, iuryl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolemethyl, thiazolmethyl, pyridinylmethyl, pyrimidinylmethyl, pyrazolylmethoxy, finylmethoxy or pyridylmethoxy, $R^3$ represents hydrogen, fluorine or chlorine or together with $R^2$ represents an alkanediyl or alkenediyl group having in each case 1 to 3 carbon atoms which optionally contains at the beginning (or end) or within the hydrocarbon chain an oxygen atom, a sulphur atom, an NH group, an N-methyl group, a carbonyl group and/or a thiocarbonyl group, and Z represents in each case monocyclic or bicyclic, saturated or unsaturated heterocyclyl, heterocyclylamino or heterocyclylimino having in each case 2 to 5 carbon atoms and 1 to 3 nitrogen atoms in the heterocyclic ring system, which optionally additionally contains an oxygen atom or sulphur atom and/or optionally up to two groups from the series —CO—, —CS—, —SO— and/or $SO_2$—, and which is optionally substituted by one or more groups from the series nitro, hydroxyl, amino, cyano, carboxyl, carbamoyl, thiocarbamoyl, fluorine, chlorine, bromine; methyl, ethyl, n- or i-propyl, n-, i-, s- or t-butyl, (which are optionally substituted by fluorine, chlorine, methoxy or ethoxy); propenyl, butenyl, propinyl or butinyl (which are in each case optionally substituted by fluorine or chlorine); methoxy, ethoxy, n- or i-propoxy, n-, i-, s- or t-butoxy, methoxy-carbonyl or ethoxycarbonyl (which are in each case optionally substituted by fluorine, chlorine, methoxy or ethoxy); propenyloxy, butenyloxy, propinyloxy or butinyloxy (which are optionally substituted by fluorine or chlorine); methylthio, ethylthio, n- or i-propylthio, n-, i-, s- or t-butylthio, propenylthio, butenyl-thio, propinylthio or butinylthio (which are in each case optionally substituted by fluorine or chlorine); methylamino, ethylamino, n- or i-propylamino, n-, i-, s- or t-butylamino, dimethylamino or diethylamino; cyclopropyl, cyclobutyl, cyclopentyl, cyclohexyl, cyclopropylmethyl, cyclobutylmethyl, cyclopentylmethyl or cyclohexylmethyl (which are in each case optionally substituted by fluorine, chlorine, methyl, ethyl, n- or i-propyl), phenyl, phenoxy, phenylthio, phenylsulphinyl, phenylsulphonyl, or phenylamino (which are in each case optionally substituted by nitro, cyano, fluorine, chlorine, bromine, methyl, ethyl, n- or i-propyl, trifluoromethyl, methoxy, ethoxy, n- or i-propoxy, difluoro-methoxyi trifluoromethoxy, methoxycarbonyl or ethoxycarbonyl).

Very particularly preferred groups of compounds of the formula (I) are the compounds of the formulae (Ia), (Ib) and (Ic) drawn below

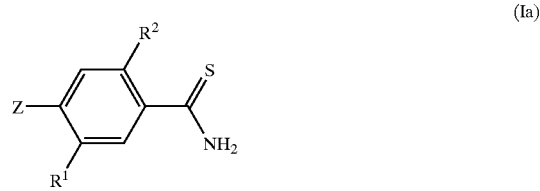

(Ia)

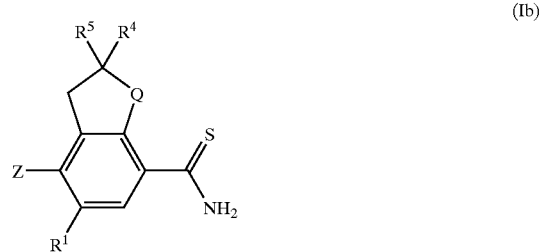

(Ib)

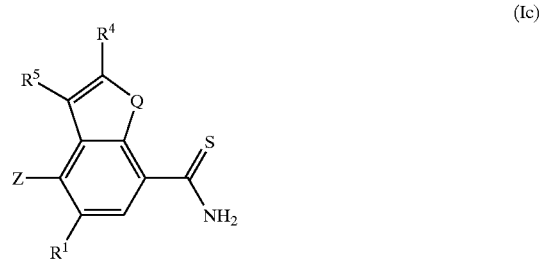

(Ic)

where $R^1$, $R^2$ and Z have the meanings indicated above as particularly preferred, $R^4$ and $R^5$ are identical or different and independently of one another in each case individually represent hydrogen, fluorine, chlorine, methyl or ethyl— or in the formula (Ib) can also together represent oxygen or sulphur— and Q represents oxygen, sulphur, N-methyl or N-ethyl.

Z in the general formulae (I) and ((Ia), (Ib) and (Ic) represents in particular the heterocyclic groups listed below

($Z^1$)

($Z^2$)

-continued
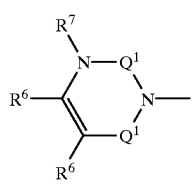 (Z³)
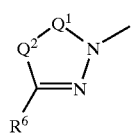 (Z⁴)
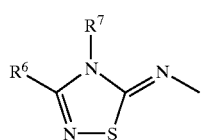 (Z⁵)
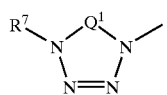 (Z⁶)
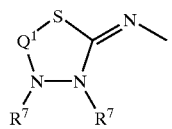 (Z⁷)
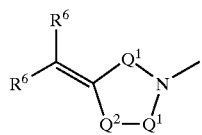 (Z⁸)
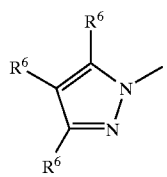 (Z⁹)
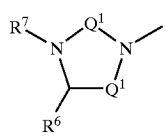 (Z¹⁰)
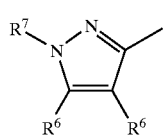 (Z¹¹)
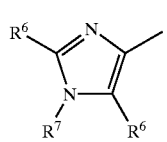 (Z¹²)
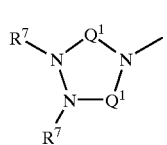 (Z¹³)
-continued
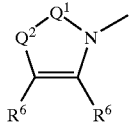 (Z¹⁴)
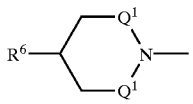 (Z¹⁵)
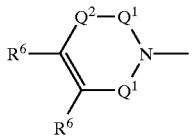 (Z¹⁶)
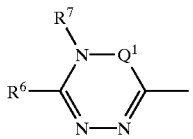 (Z¹⁷)
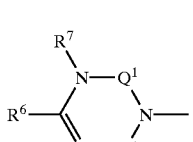 (Z¹⁸)
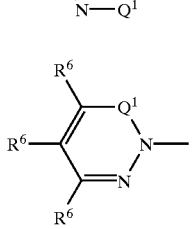 (Z¹⁹)
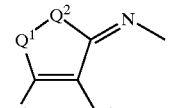 (Z²⁰)
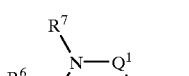 (Z²¹)
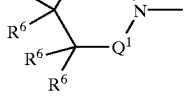 (Z²¹)
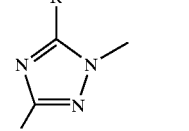 (Z²²)
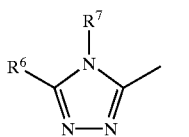 (Z²³)

-continued

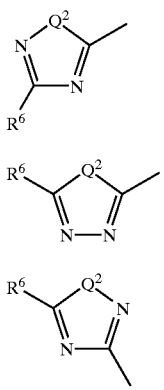

(Z²⁴)

(Z²⁵)

(Z²⁶)

where in each case $Q^1$ represents a group from the series —CO—, —CS—, —CH₂—, —CH(OH)—, —CHCl—, —CHBr—, —C(=CH₂)—, —C(=CHF)—, —C(=CF₂)—, —C(=CHCl)—, —C(=CHBr)—, —C(=CHOCHF₂)—, —C(=CHOCF₃)—, —C(=CHOCH₂CF₃)—, $Q^2$ represents oxygen, sulphur or a group from the series —CO—, —CS—, —CH₂—, —CHF—, —CF₂—, —CHCl—, —CHBr—, —CHOCHF₂—, —CHOCF₃—, —CHOCH₂CF₃—, $R^6$ represents hydrogen, amino, nitro, cyano, carboxyl, carbamoyl, fluorine, chlorine, bromine, methyl, ethyl, n- or i-propyl, cyclopropyl, difluoromethyl, trifluoromethyl, chlorodifluoromethyl, methoxy, ethoxy, n- or i-propoxy, difluoromethoxy, trifluoromethoxy, chlorodifluoromethoxy, methylthio, ethylthio, n- or i-propylthio, difluoromethylthio, trifluoromethylthio, chlorodifluoromethylthio, methylamino, ethylamino, n- or i-propylamino, dimethylamino, diethylamino, methoxycarbonyl or ethoxycarbonyl, and $R^7$ represents hydrogen, hydroxyl, amino, cyano, methyl, ethyl, n- or i-propyl, difluoromethyl, methoxy, ethoxy, n- or i-propoxy, or where optionally two adjacent groups—$R^6$ and $R^6$ or $R^7$ and $R^6$ or $R^6$ and $R^7$— together represent in each case optionally fluorine-, chlorine-, bromine-, methyl-, ethyl-, n- or i-propyl-substituted alkanediyl or alkenediyl having in each case up to 4 carbon atoms which is optionally interrupted by oxygen, sulphur or a group from the series —SO—, SO₂—, —N(CH₃)— or N(C₂H₅)— at the beginning (or at the end) or within the hydrocarbon chain.

The definitions of radicals listed above, indicated in general or in ranges of preference, apply both to the end products of the formula (I) and, correspondingly, to the respective starting materials and intermediates required for preparation. These radical definitions can be combined as desired with one another, which therefore includes any desired combinations between the indicated ranges of preferred compounds.

Examples of the compounds of the formula (I) according to the invention are listed in the groups below.

Group 1

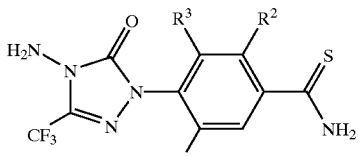

(IA-1)

In this formula, $R^1$, $R^2$ and $R^3$ have the meanings indicated in the following list:

| Synthesis Ex. No. | $R^1$ | $R^2$ | $R^3$ |
|---|---|---|---|
| 1 | H | F | H |
| 2 | H | Cl | H |
| 3 | H | Cl | Cl |
| 4 | Cl | F | H |
| 5 | F | F | H |
| 6 | F | F | Cl |
| 7 | F | CH₃ | H |
| 8 | F | C₂H₅ | H |
| 9 | F | —CH₂Cl | H |
| 10 | F | F | F |
| 11 | F | —NHC₂H₅ | H |
| 12 | F | —CH₂CN | H |
| 13 | F | —N(CH₃)SO₂C₂H₅ | H |
| 14 | Cl | —N(CH₃)SO₂C₂H₅ | H |
| 15 | Cl | —N(CH₃)SO₂C₂H₅ | Cl |
| 16 | F | —NH—COCF₃ | H |
| 17 | F | —OH | H |
| 18 | Cl | —OH | H |
| 19 | F | —CH(CH₃)₂ | H |
| 20 | F | —NH—SO₂—CH₃ | H |
| 21 | F | —SO₂—CH₃ | H |
| 22 | F | —SO₂—O—CH₃ | H |
| 23 | F | —SO₂—NH—CH₃ | H |
| 24 | F | —COOCH₃ | H |
| 25 | F | —CO—NH—CH₃ | H |
| 26 | Cl | —COOCH₃ | Cl |
| 27 | Cl | —COOC₂H₅ | H |
| 28 | F | —O—C₂H₅ | H |
| 29 | F | —N(C₂H₅)SO₂C₂H₅ | H |
| 30 | F | —N(SO₂CH₃)₂ | H |
| 31 | F | —CO—N(CH₃)₂ | H |
| 32 | F | —S—CH₂—C≡CH | H |
| 33 | Cl | —S—CH₂—C≡CH | F |
| 34 | F | —S—CH₂—C≡CH | Cl |
| 35 | F | —O—CH(CH₃)—C≡CH | H |
| 36 | F | —S—CH₂—COOCH₃ | H |
| 37 | F | —O—CH₂CH₂—OCH₃ | H |
| 38 | F | —O(CH₂CH₂O)₂CH₃ | H |
| 39 | F | —O—CH₂—CH=CH₂ | H |
| 40 | F | —O—CH₂—C≡CH | H |
| 41 | F | —SH | H |
| 42 | F | —S—CH₃ | H |
| 43 | F | —S—C₂H₅ | H |
| 44 | F | —S—CH(CH₃)₂ | H |
| 45 | F | —O—CH₂—CF₃ | H |
| 46 | F | —O—CH(CH₂F)₂ | H |
| 47 | F | —OCH(CH₃)COOC₂H₅ | H |
| 48 | F | —OCH(CH₃)COOCH₂C≡CH | H |
| 49 | F | —NH—SO₂C₂H₅ | H |
| 50 | Cl | —NH—SO₂C₂H₅ | H |
| 51 | F | —NH—SO₂C₂H₅ | Cl |

-continued

| Synthesis Ex. No. | R¹ | R² | R³ |
|---|---|---|---|
| 52 | F | —NH—SO$_2$CH(CH$_3$)$_2$ | H |
| 53 | F | —NH—SO$_2$C$_4$H$_9$ | H |
| 54 | F | —N=CH—OC$_2$H$_5$ | H |
| 55 | F | —N=C(CH$_3$)OC$_2$H$_4$ | H |
| 56 | F | —N=C(OCH$_3$)$_2$ | H |
| 57 | F | —N=CH—N(CH$_3$)$_2$ | H |
| 58 | F | —SCN | H |
| 59 | F | —SO$_2$Cl | H |
| 60 | F | —O—CS—N(CH$_3$)$_2$ | H |
| 61 | F | —S—CO—N(CH$_3$)$_2$ | H |
| 62 | F | —NH—P(O)(CH$_3$)OC$_2$H$_5$ | H |
| 63 | F | —NH—P(O)(OCH$_5$)$_2$ | H |
| 64 | F | —NH—COC$_2$H$_5$ | H |
| 65 | F | —N(CH$_3$)COCF$_3$ | H |
| 66 | F | —NH—COCH(CH$_3$)$_2$ | H |
| 67 | F | —NH—CO—CO—C(CH$_3$)$_3$ | H |
| 68 | F | —NH—CO—NH$_2$ | H |
| 69 | F | —NH—CO—NHCH$_3$ | H |
| 70 | F | —NH—CO—N(CH$_3$)$_2$ | H |
| 71 | F | —N(COCH$_3$)$_2$ | H |
| 72 | F | —NH—COCH(CH$_3$)Cl | H |
| 73 | F | —S—CH$_2$—CH=CH$_2$ | H |
| 74 | Cl | —S—CH$_2$—CH=CH$_2$ | H |
| 75 | F | —S—CH(CH$_3$)C≡CH | H |
| 76 | F | —S—CH(CH$_3$)COOC$_2$H$_5$ | H |
| 77 | F | —S(O)—CH$_3$ | H |
| 78 | F |  | H |
| 79 | F |  | H |
| 80 | F |  | H |
| 81 | F |  | H |
| 82 | F |  | H |
| 83 | F |  | H |
| 84 | F | —O—CH$_2$—CN | H |
| 85 | F | —O—SO$_2$—CH$_3$ | H |
| 86 | F | —OCH$_2$—CH(Cl)=CH$_2$ | H |
| 87 | F | —O—CH$_2$—COOCH$_3$ | H |
| 88 | F | —O—CHF$_2$ | H |
| 89 | F | —OCOOCH$_2$CH$_2$Cl | H |
| 90 | F | —OCH$_2$P(O)(OC$_2$H$_5$)$_2$ | H |
| 91 | Cl | —O—CH(CH$_3$)P(O)(OC$_2$H$_5$)$_2$ | H |
| 92 | F |  | H |
| 93 | F |  | H |
| 94 | F | —O—N(C$_2$H$_5$)$_2$ | H |
| 95 | F |  | H |
| 96 | F |  | H |
| 97 | F |  | Cl |
| 98 | Cl |  | H |
| 99 | F |  | F |
| 100 | F |  | H |
| 101 | F |  | H |
| 102 | F |  | H |
| 103 | F | —NCH(CH$_3$)$_2$SO$_2$C$_2$H$_5$ | H |
| 104 | F | —N(CH$_3$)SO$_2$CH(CH$_3$)$_2$ | H |
| 105 | H | —N(CH$_3$)SO$_2$C$_2$H$_5$ | Cl |
| 106 | Cl | —N(CH$_3$)SO$_2$C$_4$H$_9$ | H |
| 107 | F | —N(CH$_3$)SO$_2$C$_2$H$_5$ | H |
| 108 | F | —N(CH$_3$)SO$_2$CH$_3$ | H |
| 109 | F | —N(SO$_2$C$_2$H$_5$)$_2$ | H |
| 110 | F | —N(SO$_2$CH$_3$)SO$_2$C$_2$H$_5$ | H |
| 111 | F |  | H |
| 112 | F | —N(CH$_3$)$_2$ | H |
| 113 | F | —NH$_2$ | H |
| 114 | Cl | —NH$_2$ | H |
| 115 | Cl | —O—CH(CH$_3$)$_2$ | H |
| 116 | F | —O—CH(CH$_3$)$_2$ | H |
| 117 | F |  | H |
| 118 | Cl |  | H |
| 119 | F | —O—CH$_2$—COOC$_2$H$_5$ | H |
| 120 | F | —S—CH$_2$—COOCH$_3$ | H |
| 121 | F | —S—CH$_2$—COOC$_2$H$_5$ | H |
| 122 | Cl | —S—CH$_2$—COOC$_2$H$_5$ | H |
| 123 | F | —CH$_2$—CH(Cl)COOCH$_3$ | H |

-continued

| Synthesis Ex. No. | R¹ | R² | R³ |
|---|---|---|---|
| 124 | F | —CH₂—CH(Cl)COOC₂H₅ | H |
| 125 | F | —CH₂—CH(Cl)CONHC₂H₅ | H |
| 126 | Cl | —CH₂—CH(Cl)CONHC₂H₅ | H |
| 127 | Cl | —CH₂CH(Cl)CONHCH(CH₃)₂ | H |
| 128 | F | —CH₂CH(Cl)CONHCH(CH₃)₂ | H |
| 129 | F | —COOC₃H₇-i | H |

Group 2

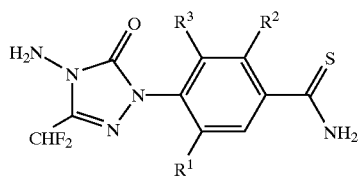
(IA-2)

In this formula, R¹, R² and R³ have, for example, the meanings indicated above in Group 1.

Group 3

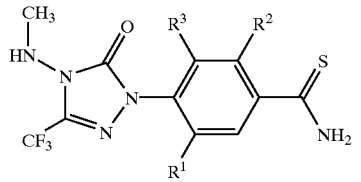
(IA-3)

In this formula, R¹, R² and R³ have, for example, the meanings indicated above in Group 1.

Group 4

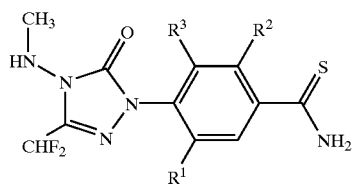
(IA-4)

In this formula, R¹, R² and R³ have, for example, the meanings indicated above in Group 1.

Group 5

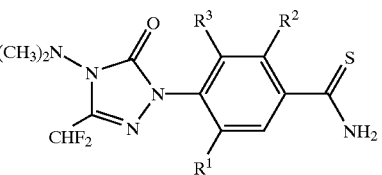
(IA-5)

In this formula, R¹, R² and R³ have, for example, the meanings indicated above in Group 1.

Group 6

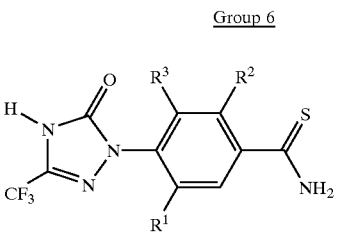
(IA-6)

In this formula, R¹, R² and R³ have, for example, the meanings indicated above in Group 1.

Group 7

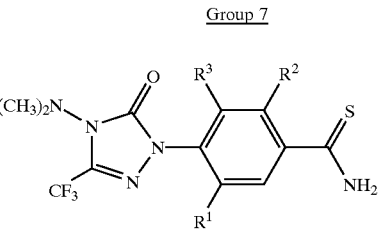
(IA-7)

In this formula, R¹, R² and R³ have, for example, the meanings indicated above in Group 1.

Group 8

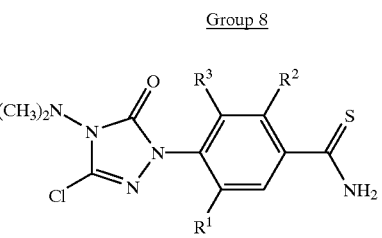
(IA-8)

In this formula, R¹, R² and R³ have, for example, the meanings indicated above in Group 1.

Group 9

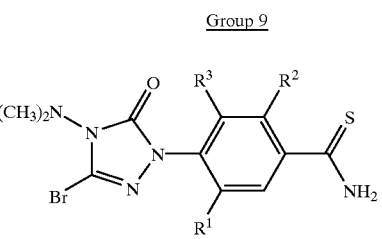
(IA-9)

In this formula, R¹, R² and R³ have, for example, the meanings indicated above in Group 1.

Group 10

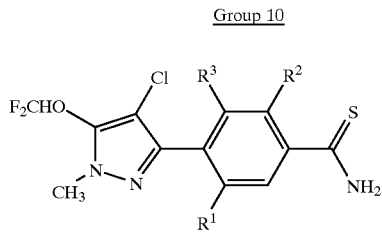
(IA-10)

In this formula, $R^1$, $R^2$ and $R^3$ have, for example, the meanings indicated above in Group 1.

Group 11

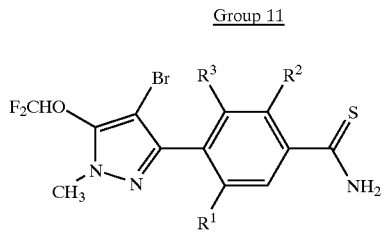
(IA-11)

In In this formula, $R^1$, $R^2$ and $R^3$ have, for example, meanings indicated above in Group 1.

Group 12

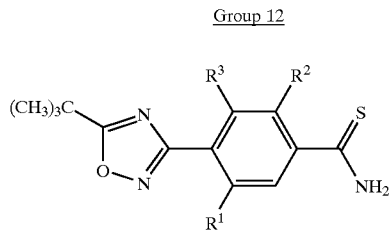
(IA-12)

In this formula, $R^1$, $R^2$ and $R^3$ have, for example, the meanings indicated above in Group 1.

Group 13

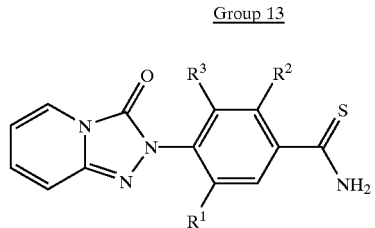
(IA-13)

In this formula, $R^1$, $R^2$ and $R^3$ have, for example, the meanings indicated above in Group 1.

Group 14

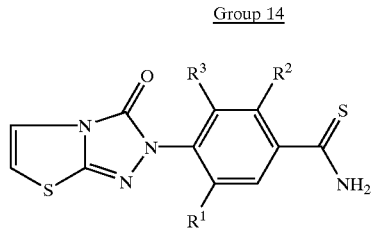
(IA-14)

In this formula, $R^1$, $R^2$ and $R^3$ have, for example, the meanings indicated above in Group 1.

Group 15

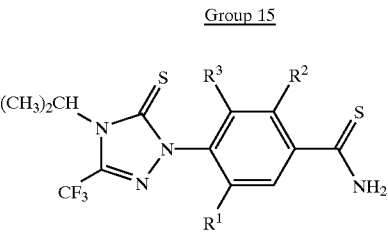
(IA-15)

In this formula, $R^1$, $R^2$ and $R^3$ have, for example, the meanings indicated above in Group 1.

Group 16

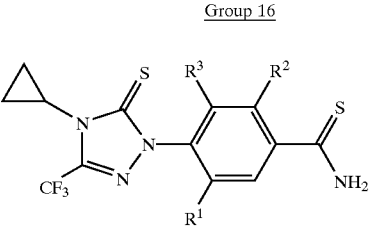
(IA-16)

In this formula, $R^1$, $R^2$ and $R^3$ have, for example, the meanings indicated above in Group 1.

Group 17

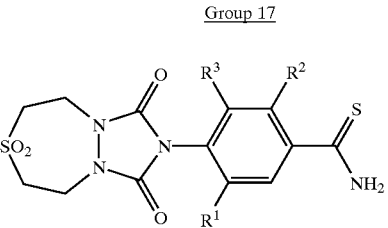
(IA-17)

In this formula, $R^1$, $R^2$ and $R^3$ have, for example, the meanings indicated above in Group 1.

Group 18

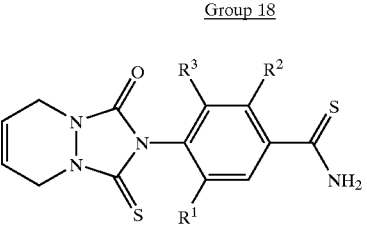
(IA-18)

In this formula, $R^1$, $R^2$ and $R^3$ have, for example, the meanings indicated above in Group 1.

Group 19

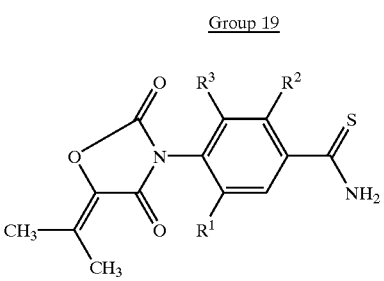
(IA-19)

In this formula, $R^1$, $R^2$ and $R^3$ have, for example, the meanings indicated above in Group 1.

Group 20

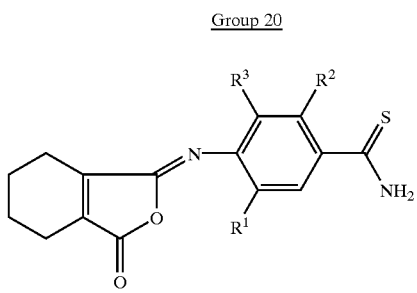
(IA-20)

In this formula, $R^1$, $R^2$ and $R^3$ have, for example, the meanings indicated above in Group 1.

Group 21

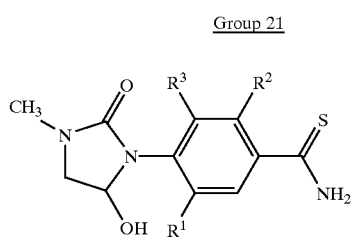
(IA-21)

In this formula, $R^1$, $R^2$ and $R^3$ have, for example, the meanings indicated above in Group 1.

Group 22

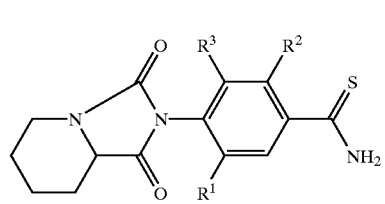
(IA-22)

In this formnula, $R^1$, $R^2$ and $R^3$ have, for example, the meanings indicated above in Group 1.

Group 23

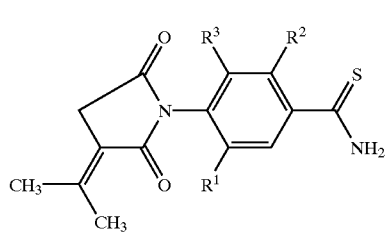
(IA-23)

In this formula, $R^1$, $R^2$ and $R^3$ have, for example, the meanings indicated above in Group 1.

Group 24

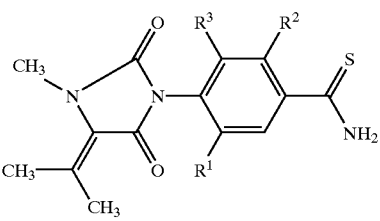
(IA-24)

In this formula, $R^1$, $R^2$ and $R^3$ have, for example, the meanings indicated above in Group 1.

Group 25

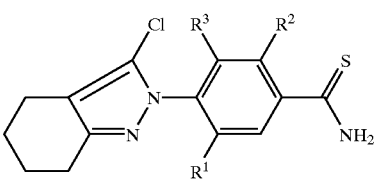
(IA-25)

In this formula, $R^1$, $R^2$ and $R^3$ have, for example, the meanings indicated above in Group 1.

Group 26

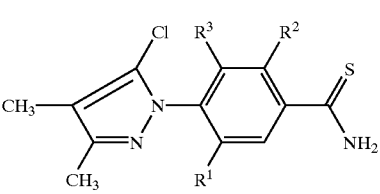
(IA-26)

In this formula, $R^1$, $R^2$ and $R^3$ have, for example, the meanings indicated above in Group 1.

Group 27

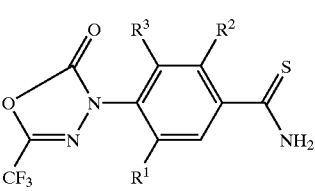
(IA-27)

In this formula, $R^1$, $R^2$ and $R^3$ have, for example, the meanings indicated above in Group 1.

Group 28

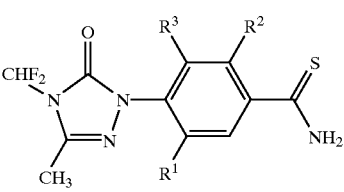
(IA-28)

Group 29

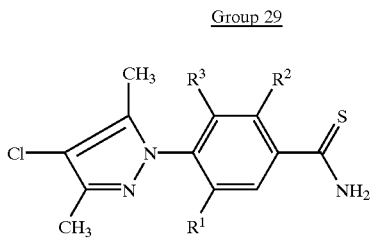
(IA-29)

In this formula, $R^1$, $R^2$ and $R^3$ have, for example, the meanings indicated above in Group 1.

Group 30

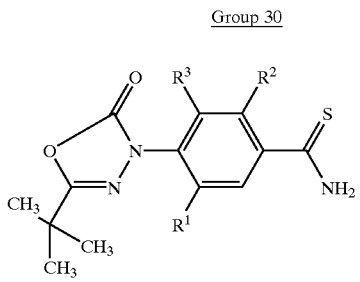
(IA-30)

In this formula, $R^1$, $R^2$ and $R^3$ have, for example, the meanings indicated above in Group 1.

Group 31

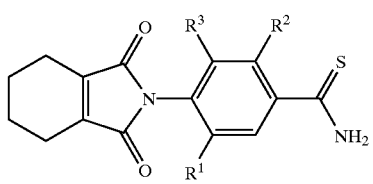
(IA-31)

In this formula, $R^1$, $R^2$ and $R^3$ have, for example, the meanings indicated above in Group 1.

Group 32

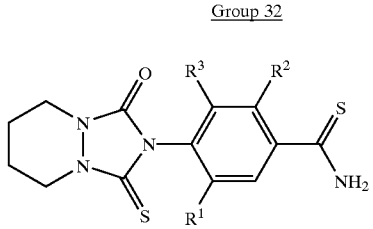
(IA-32)

In this formula, $R^1$, $R^2$ and $R^3$ have, for example, the meanings indicated above in Group 1.

Group 33

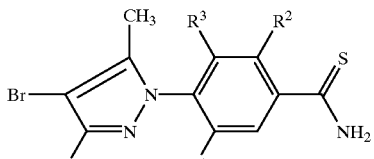
(IA-33)

In this formula, $R^1$, $R^2$ and $R^3$ have, for example, the meanings indicated above in Group 1.

Group 34

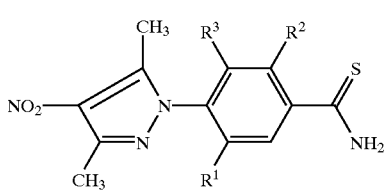
(IA-34)

In this formula, $R^1$, $R^2$ and $R^3$ have, for example, the meanings indicated above in Group 1.

Group 35

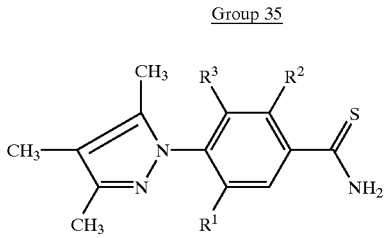
(IA-35)

In this formula, $R^1$, $R^2$ and $R^3$ have, for example, the meanings indicated above in Group 1.

Group 36

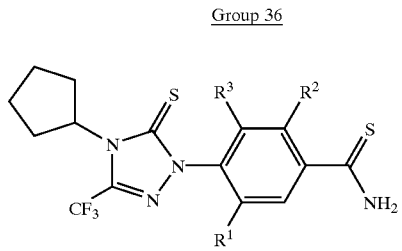
(IA-36)

In this formula, $R^1$, $R^2$ and $R^3$ have, for example, the meanings indicated above in Group 1.

Group 37

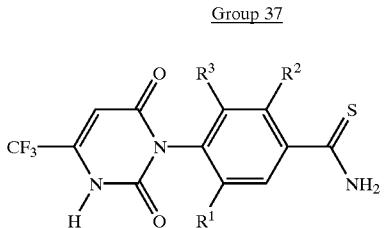
(IA-37)

In this formula, $R^1$, $R^2$ and $R^3$ have, for example, the meanings indicated above in Group 38

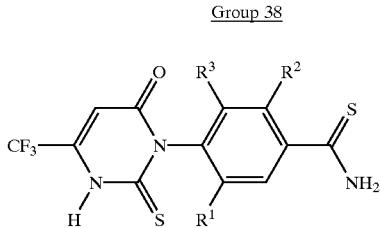

(IA-38)

In this formula, $R^1$, $R^2$ and $R^3$ have, for example, the meanings indicated above in Group 1.

Group 39

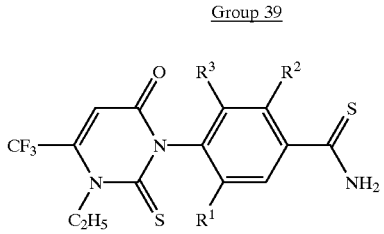

(IA-39)

In this formula, $R^1$, $R^2$ and $R^3$ have, for example, the meanings indicated above in Group 1.

Group 40

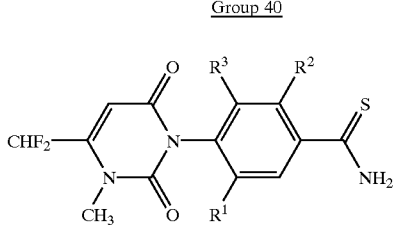

(IA-40)

In this formula, $R^1$, $R^2$ and $R^3$ have, for example, the meanings indicated above in Group 1.

Group 41

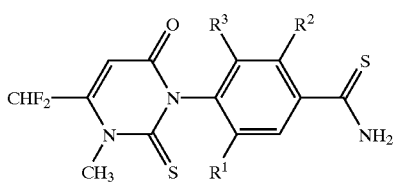

(IA-41)

In this formula, $R^1$, $R^2$ and $R^3$ have, for example, the meanings indicated above in Group 1.

Group 42

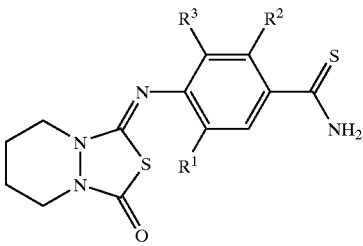

(IA-42)

In this formula, $R^1$, $R^2$ and $R^3$ have, for example, the meanings indicated above in Group 1.

Group 43

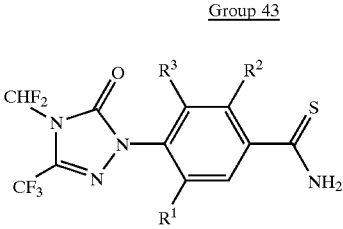

(IA-43)

In this formula, $R^1$, $R^2$ and $R^3$ have, for example, the meanings indicated above in Group 1.

Group 44

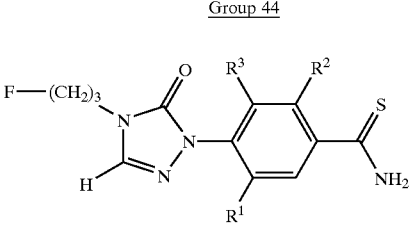

(IA-44)

In this formula, $R^1$, $R^2$ and $R^3$ have, for example, the meanings indicated above in Group 1.

Group 45

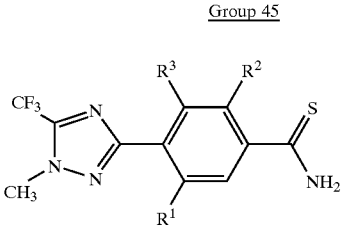

(IA-45)

In this formula, $R^1$, $R^2$ and $R^3$ have, for example, the meanings indicated above in Group 1.

Group 46

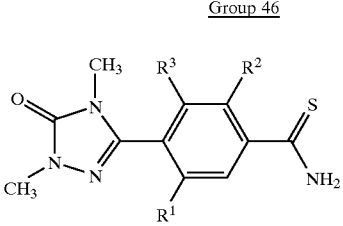

(IA-46)

Group 47

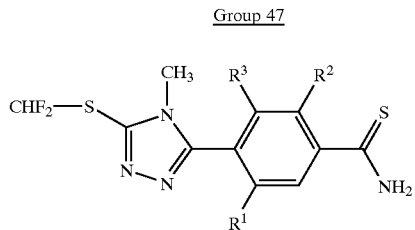
(IA-47)

In this formula, $R^1$, $R^2$ and $R^3$ have, for example, the meanings indicated above in Group 1.

Group 48

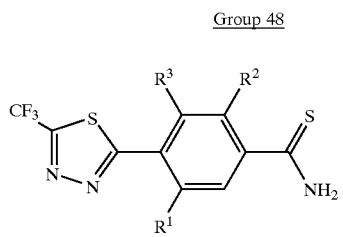
(IA-48)

In this formula, $R^1$, $R^2$ and $R^3$ have, for example, the meanings indicated above in Group 1.

Group 49

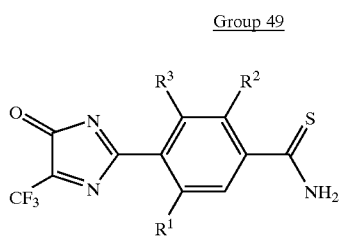
(IA-49)

In this formula, $R^1$, $R^2$ and $R^3$ have, for example, the meanings indicated above in Group 1.

Group 50

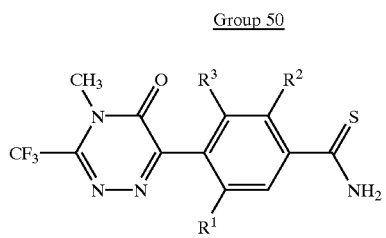
(IA-50)

In this formula, $R^1$, $R^2$ and $R^3$ have, for example, the meanings indicated above in Group 1.

Group 51

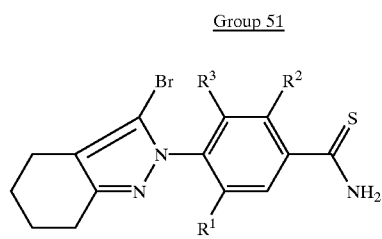
(IA-51)

In this formula, $R^1$, $R^2$ and $R^3$ have, for example, the meanings indicated above in.

Group 52

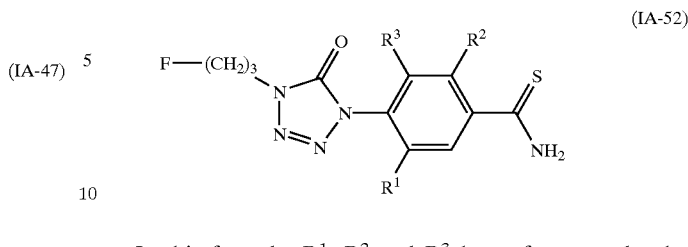
(IA-52)

In this formula, $R^1$, $R^2$ and $R^3$ have, for example, the meanings indicated above in Group 1.

Group 53

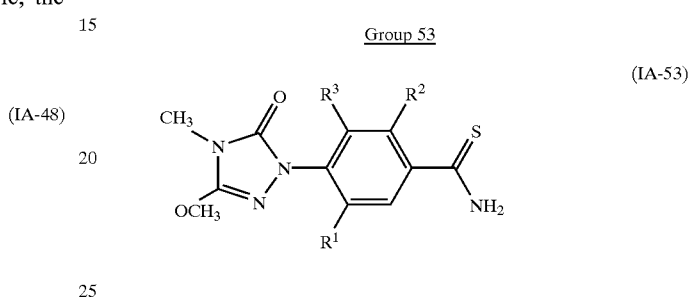
(IA-53)

In this formula, $R^1$, $R^2$ and $R^3$ have, for example, the meanings indicated above in Group 1.

Group 54

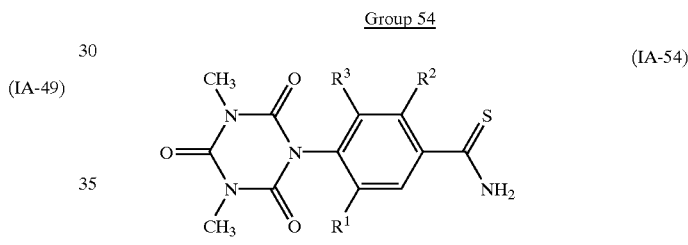
(IA-54)

In this formula, $R^1$, $R^2$ and $R^3$ have, for example, the meanings indicated above in Group 1.

Group 55

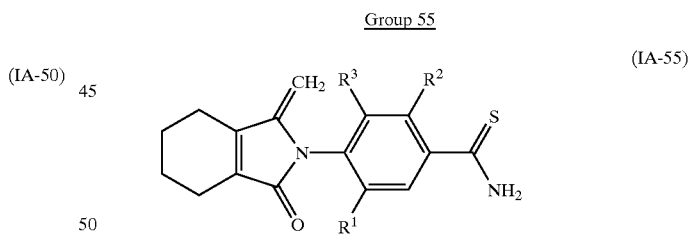
(IA-55)

In this formula, $R^1$, $R^2$ and $R^3$ have, for example, the meanings indicated above in Group 1.

Group 56

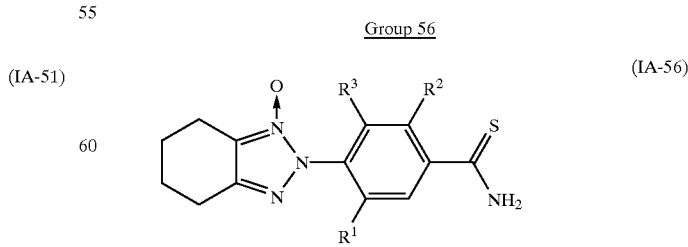
(IA-56)

In this formula, $R^1$, $R^2$ and $R^3$ have, for example, the meanings indicated above in Group 1.

Group 57

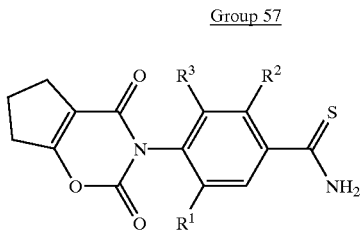
(IA-57)

In this formula, $R^1$, $R^2$ and $R^3$ have, for example, the meanings indicated above in Group 1.

Group 58

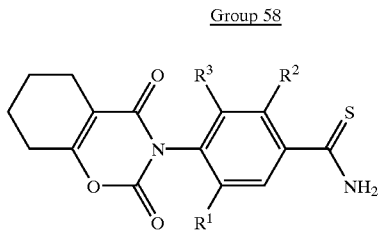
(IA-58)

In this formula, $R^1$, $R^2$ and $R^3$ have, for example, the meanings indicated above in Group 1.

Group 59

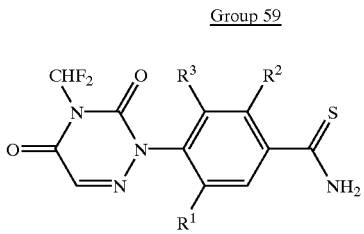
(IA-59)

In this formula, $R^1$, $R^2$ and $R^3$ have, for example, the meanings indicated above in Group 1.

Group 60

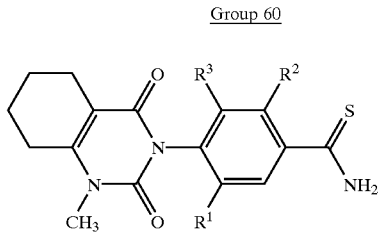
(IA-60)

In this formula, $R^1$, $R^2$ and $R^3$ have, for example, the meanings indicated above in Group 1.

Group 61

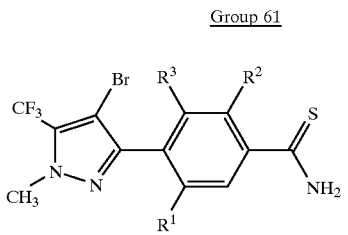
(IA-61)

In this formula, $R^1$, $R^2$ and $R^3$ have, for example, the meanings indicated above in Group 1.

Group 62

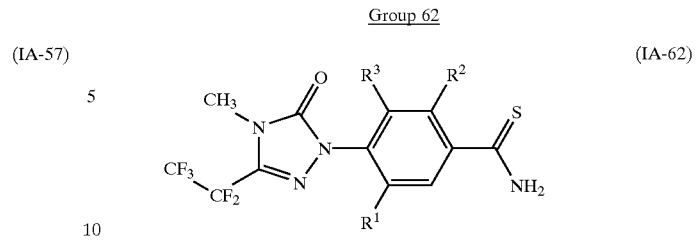
(IA-62)

In this formula, $R^1$, $R^2$ and $R^3$ have, for example, the meanings indicated above in Group 1.

Group 63

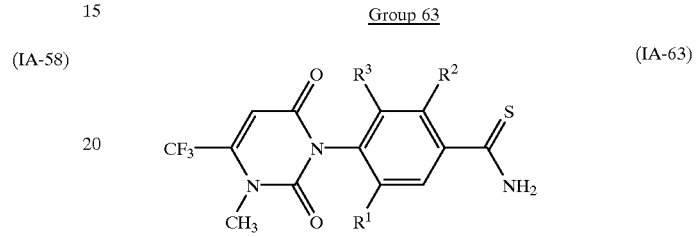
(IA-63)

In this formula, $R^1$, $R^2$ and $R^3$ have, for example, the meanings indicated above in Group 1.

Group 64

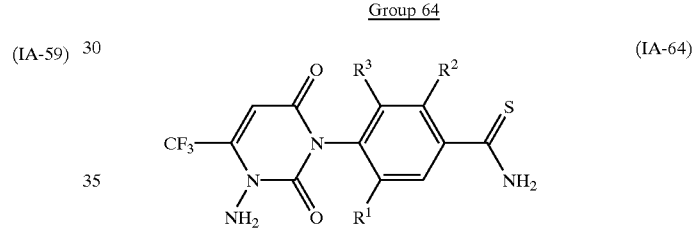
(IA-64)

In this formula, $R^1$, $R^2$ and $R^3$ have, for example, the meanings indicated above in Group 1.

Group 65

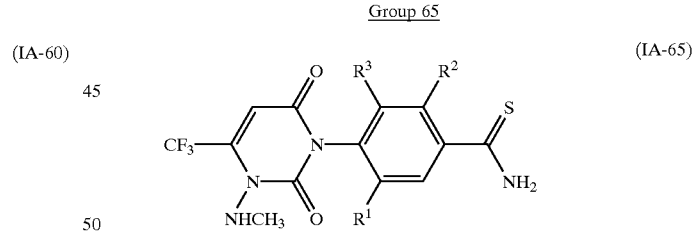
(IA-65)

In this formula, $R^1$, $R^2$ and $R^3$ have, for example, the meanings indicated above in Group 1.

Group 66

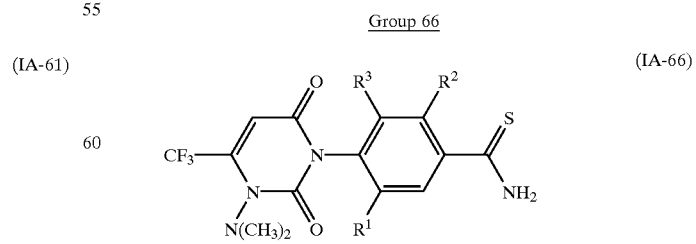
(IA-66)

In this formula, $R^1$, $R^2$ and $R^3$ have, for example, the meanings indicated above in Group 1.

Group 67

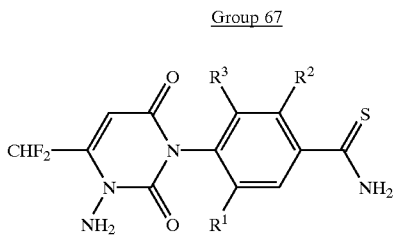
(IA-67)

In this formula, $R^1$, $R^2$ and $R^3$ have, for example, the meanings indicated above in Group 1.

Group 68

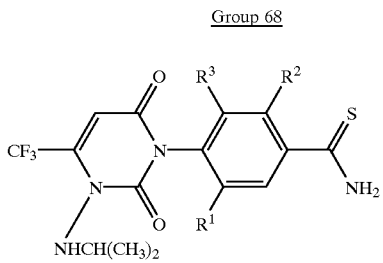
(IA-68)

In this formula, $R^1$, $R^2$ and $R^3$ have, for example, the meanings indicated above in Group 1.

Group 69

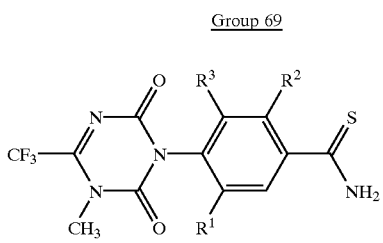
(IA-69)

In this formula, $R^1$, $R^2$ and $R^3$ have, for example, the meanings indicated above in Group 1.

Group 70

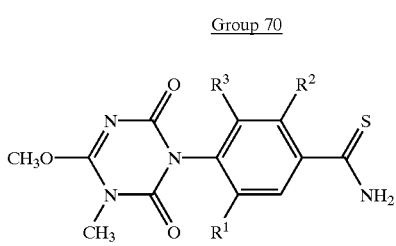
(IA-70)

In this formula, $R^1$, $R^2$ and $R^3$ have, for example, the meanings indicated above in Group 1.

Group 71

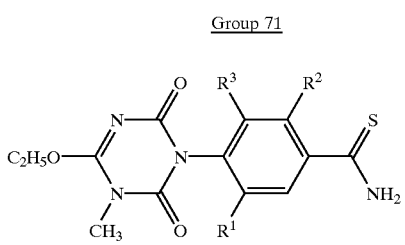
(IA-71)

In this formula, $R^1$, $R^2$ and $R^3$ have, for example, the meanings indicated above in Group 1.

Group 72

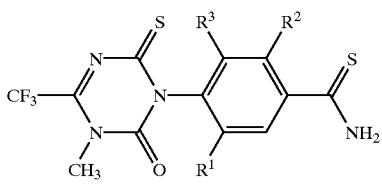
(IA-72)

In this formula, $R^1$, $R^2$ and $R^3$ have, for example, the meanings indicated above in Group 1.

Group 73

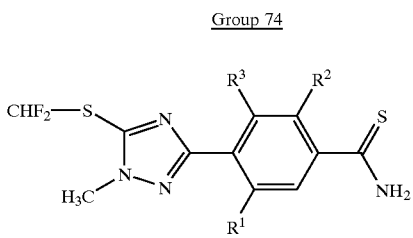
(IA-73)

In this fonnula, $R^1$, $R^2$ and $R^3$ have, for example, the meanings indicated above in Group 1.

Group 74

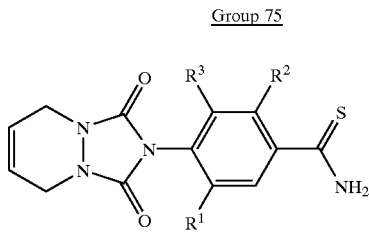
(IA-74)

In this formula, $R^1$, $R^2$ and $R^3$ have, for example, the meanings indicated above in Group 1.

Group 75

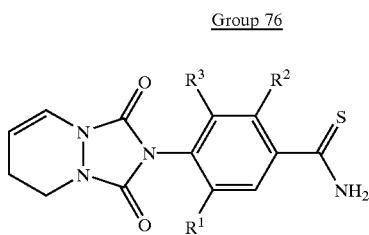
(IA-75)

In this formula, $R^1$, $R^2$ and $R^3$ have, for example, the meanings indicated above in Group 1.

Group 76

(IA-76)

In this formula, $R^1$, $R^2$ and $R^3$ have, for example, the meanings indicated above in Group 1.

Group 77

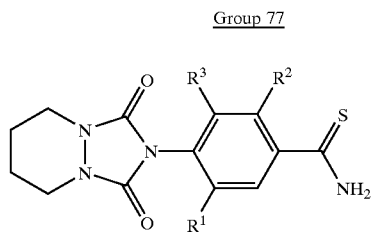

(IA-77)

In this formula, $R^1$, $R^2$ and $R^3$ have, for example, the meanings indicated above in Group 1.

Group 78

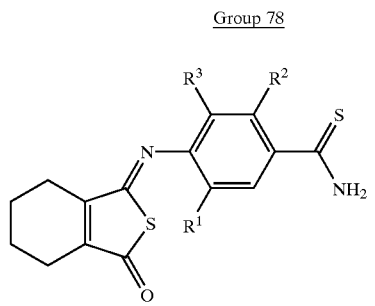

(IA-78)

In this formula, $R^1$, $R^2$ and $R^3$ have, for example, the meanings indicated above in Group 1.

Group 79

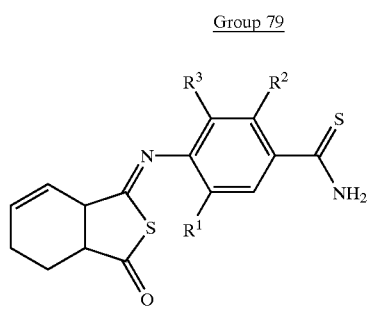

(IA-79)

In this formula, $R^1$, $R^2$ and $R^3$ have, for example, the meanings indicated above in Group 1.

Table 80

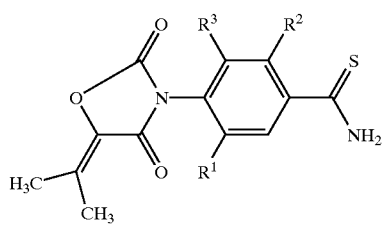

(IA-80)

In this formula, $R^1$, $R^2$ and $R^3$ have, for example, the meanings indicated above in Group 1.

Group 81

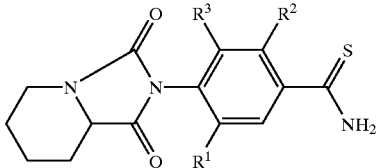

(IA-81)

In this formula, $R^1$, $R^2$ and $R^3$ have, for example, the meanings indicated above in Group 1.

Group 82

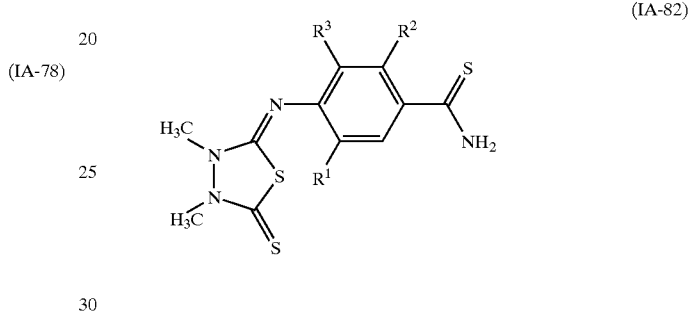

(IA-82)

In this formula, $R^1$, $R^2$ and $R^3$ have, for example, the meanings indicated above in Group 1.

Group 83

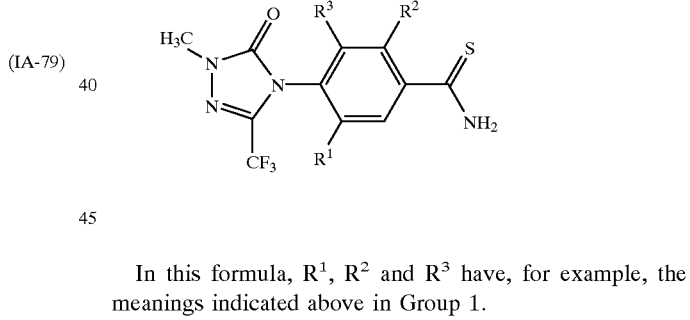

(IA-83)

In this formula, $R^1$, $R^2$ and $R^3$ have, for example, the meanings indicated above in Group 1.

Group 84

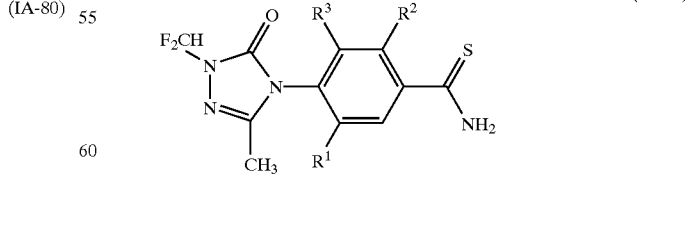

(IA-84)

In this formula, $R^1$, $R^2$ and $R^3$ have, for example, the meanings indicated above in Group 1.

Group 85

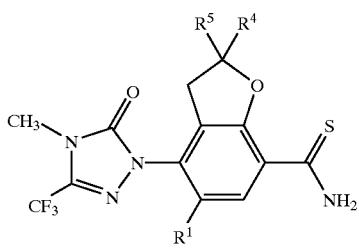

(IB-1)

In this formula, $R^1$, $R^4$ and $R^5$ have, the meanings indicated in the following list:

| Ex. No. | $R^1$ | $R^4$ | $R^5$ |
|---|---|---|---|
| 1 | F | $CH_3$ | $CH_3$ |
| 2 | Cl | $CH_3$ | $CH_3$ |
| 3 | H | $CH_3$ | $CH_3$ |
| 4 | F | Cl | $CH_3$ |
| 5 | F | Cl | Cl |
| 6 | F | $C_2H_5$ | $CH_3$ |

Group 86

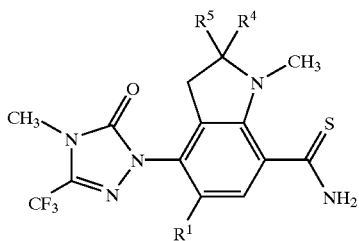

(IB-2)

In this formula, $R^1$, $R^4$ and $R^5$ have, for example, the meanings indicated above in Group 85.

Group 87

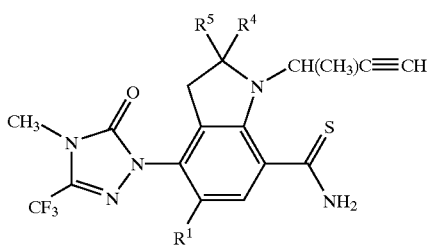

(IB-3)

In this formula, $R^1$, $R^4$ and $R^5$ have, for example, the meanings indicated above in Group 85.

Group 88

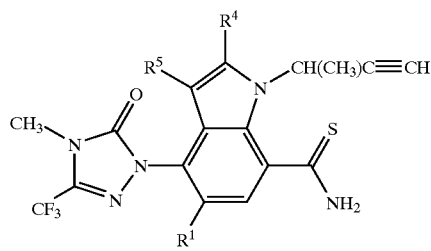

(IC-1)

In this formula, $R^1$, $R^4$ and $R^5$ have, for example, the meanings indicated above in Group 85.

Group 89

(IC-2)

In this formula, $R^1$, $R^4$ and $R^5$ have, for example, the meanings indicated above in Group 85.

Using, for example, 2-(2-fluoro-4-cyano-5-methoxyphenyl)-4-methyl-5-difluoromethyl-2,4-dihydro-3H-1,2,4-triazol-3-one and hydrogen sulphide as starting materials, the course of reaction of the process according to the invention can be illustrated by the following equation:

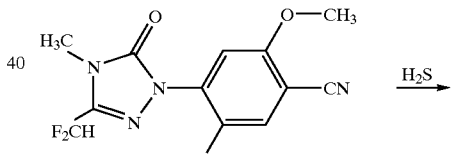

A general definition of the substituted aromatic nitriles to be used as starting materials in the process according to the invention for the preparation of the compounds of the general formula (I) is given by the formula (II). In the formula (II), $R^1$, $R^2$, $R^3$ and Z preferably or in particular have those meanings which have already been indicated above, in connection with the description of the compounds of the formula (I), as preferred or, respectively, as particularly preferred for $R^1$, $R^2$, $R^3$ and Z.

The starting materials of the formula (II) are known and/or can be prepared by known processes (cf. EP-A 370332; DE-A 4238125; DE-A 4303376; U.S. Pat. No. 5084084; Preparation Examples).

Suitable diluents for carrying out the process according to the invention are the customary organic solvents. These include, in particular, aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran or ethylene glycol dimethyl or diethyl ether; ketones, such as acetone, butanone or methyl isobutyl ketone; nitrites, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, azines, such as pyridine, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water, or pure water.

The process according to the invention is preferably carried out in the presence of a suitable reaction auxiliary. Suitable such auxiliaries are all customary inorganic or organic bases. These include, for example, alkaline earth metal or alkali metal hydrides, hydroxides, amides, alcoholates, acetates, carbonates or hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate and also basic organic nitrogen compounds, such as trimethylamine, triethylamine, tributylamine, N,N-dimethylaniline, pyridine, N-methylpiperidine, N,N-dimethylaminopyridine, diazabicyclooctane (DABCO), diaza-bicyclononene (DBN) or diazabicycloundecene (DBU).

The reaction temperatures when carrying out the process according to the invention can be varied within a relatively large range. It is generally carried out at temperatures between 0° C. and 100° C., preferably at temperatures between 10° C. and 80° C.

The process according to the invention is generally carried out under atmospheric pressure. However, it is also possible to operate under elevated or reduced pressure, generally between 0.1 bar and 10 bar.

To carry out the process according to the invention the starting materials of the formula (II) are introduced, generally in a suitable diluent in the presence of a reaction auxiliary, and the hydrogen slulphide or the thioacetamide is slowly metered in. The hydrogen sulphide or the thioacetamide are preferably employed in a relatively large excess. The reaction mixture is stirred for a number of hours at the particular temperature required. Working up in the process according to the invention is effected in each case in accordance with customary methods (cf. the Preparation Examples).

The active compounds according to the invention can be used as defoliants, desiccants, haulm killers and, especially, as weedkillers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthernis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleura, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are particularly suitable for selective control of monocotyledon and dicotyledon weeds in monocotyledon and dicotyledon crops, both pre- and post-emergence.

To a certain extent, the compounds of the formula (I) also show a fungicidal action, for example against Pyricularia oryzae in rice.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyes such as alizarin dyes, axo dyes and metal phthalocyanine dyes, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, examples being anilides, for example, diflufenican and propanil; arylcarboxylic acids, for example dichloropicolinic acid, dicamba and picloram; aryloxyalkanoic acids, for example 2,4 D, 2,4 DB, 2,4 DP, fluroxypyr, MCPA, MCPP and triclopyr; aryloxy-phenoxy-alkanoic esters, for example diclofop(-methyl), fenoxaprop(-ethyl), fluazifop(-butyl), haloxyfop (-methyl) and quizalofop(-ethyl); azinones, for example chloridazon and norflurazon; carabamates, for example chlorpropham, desmedipham, phenmaedipham and propham; chloroacetanilides, for example alachlor, acetochlor, butachlor, metazachlor, metolachlor, pretilachlor and propachlor; dinitroanilines, for example oryzalin, pendimethalin and trifluralin; diphenyl ethers, for example acifluorfen, bifenox, chlornethoxynil (X-52), chlornitrofen, fluoroglycofen, fomesafen, halosafen, lactofen, nitrofen and oxyfluorfen; ureas, for example chlortoluron, cumyluron (JC-940), diuron, dymron (daimuron), fluormeturon, isoproturon, linuron and methabenzthiazuron; hyroxylamines, for example alloxydim, clethodim, cycloxydim, sethoxydim and tralkoxydim; imidazolinones, for example imazethapyr, imazamethabenz, imazapyr and imazaquin; nitriles, for example bromoxynil, dichlobenil and ioxynil; oxyacetamides, for example mefenacet; sulphonylureas, for example AC-014 (AC-322140), amidosulfuron, bensulfuron(-methyl), chlorimuron(-ethyl), chlorsulfuron, cinosulfuron, DPX47, HOE-404, imazosulfuiron, metsulfuron(-methyl), nicosulfuron, primisulfuron, pyrazosulfuron(-ethyl), thifensulfuiron(-methyl), triasulfuron and tribenuron(-methyl); thiocarbamates, for example butylate, cycloate, diallate, dimepiperate, EPTC, esprocarb, molinate, prosulphocarb, thiobencarb (benthiocarb) and triallate; triazines, for example atrazine, cyanazine, dimethametryn, prometryne, simazin, simetryne, terbutryne and terbutylazin; triazinones, for example hexazinon, metamitron and metribuzin; others, for example aminotriazole, benfuresate, bensulide, bentazone, benzofenap, bromobutide, butamifos, cafenstrole (CH-900), cinmethylin, clomazone, clomeprop, clopyralid, DEH-112, difenzoquat, dimethenamid, dithiopyr, ethofumesate, flumetsulam, fluorochloridone, glufosinate, glyphosate, amiprophos(-methyl), anilofos, etobenzanid (HW-52), isoxaben, KPP-314, KUH-833, KUH-911, KUH-920, MK-243, naproanilide, NSK-850, oxadiazon, piperophos, propanil, pyrazolate, pyrazoxyfen, pyributicarb, pyridate, quinchlorac, quinmerac, sulphosate and tridiphane.

Mixtures with other known active compounds, such as fuingicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the examples which follow.

PREPARATION EXAMPLES

EXAMPLE 1

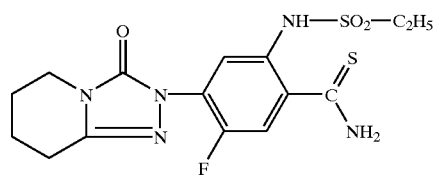

Hydrogen sulphide is passed at from 50° C. to 60° C. to saturation point into a mixture of 5.5 g (15 mmol) of 2-(4-cyano-2-fluoro-5-ethylsulphonylamino-phenyl)-5,6,7,8-tetrahydro-1,2,4-triazolo[4,3-a]pyridin-3(2H)-one, 5 ml of triethylamine and 50 ml of pyridine and the mixture is stirred at 60° C. for 30 minutes more. It is then concentrated in vacuo, the residue is stirred with 2 N hydrochloric acid and the solids are filtered off. The solid product is recrystallized from isopropanol.

4.8 g (80% of theory) of 2-(2-fluoro-5-ethylsulphonylamino4-thiocarbamoyl-phenyl)-5,6,7,8-tetrahydro-1,2,4-triazolo[4,3-a]pyridin-3(2H)-one are obtained of melting poin 220° C.

EXAMPLE 2

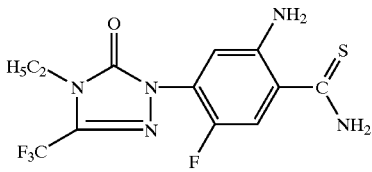

4.04 g (0.04 mol) of triethylamine are added to 6.3 g (0.02 mol) of 2-(2-fluoro-4-cyano-5-amino-phenyl)4-ethyl-5-trifluoromethyl-2,4-dihydro-3H-1,2,4-triazol-3-one in 100 ml of acetone. Hydrogen sulphide is passed in rapidly at 23° C., and the internal temperature rises to 33° C. The reaction is complete after 1 hour. The solution is concentrated on a rotary evaporator and the residue is recrystallized from isopropanol.

2.9 g (42% of theory) of 2-(2-fluoro4-thiocarbamoyl-5-amino-phenyl)4-ethyl-5-trifluoromethyl-2,4-dihydro-3H-1,2,4-triazol-3-one are obtained of melting point 161° C.

EXAMPLE 3

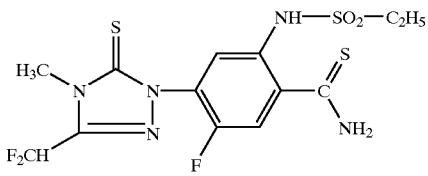

11 g (0.0276 mol) of 2-(2-fluoro-4-cyano-5-ethylsulphonylaminophenyl)-4-methyl-5-difluoromethyl-2,4-dihydro-3H-1,2,4-triazole-3-thione are stirred at 70° C. for 4.5 hours in 100 ml of pyridine while passing in hydrogen sulphide. The solution is concentrated on a rotary evaporator, the residue is stirred in water, the mixture is acidified with concentrated hydrochloric acid, and precipitated product is filtered off, washed with water and recrystallized from isopropanol.

9 g (77% of theory) of 2-(2-fluoro4-thiocarbamoyl-5-ethylsulphonylaminophenyl)4-methyl-5-difluoromethyl-2,4-dihydro-3H-1,2,4-triazole-3-thione are obtained of melting point 183° C.

In analogy to Preparation Examples 1, 2 and 3 and in accordance with the general description of the preparation process according to the invention it is also possible, for example, to prepare the compounds of the formula (I) listed in Table 1 below.

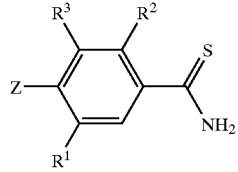

(I)

TABLE 1

Examples of the compounds of the formula (I)

| Ex. No. | $R^1$ | $R^2$ | $R^3$ | Z | Melting point (° C.) |
|---|---|---|---|---|---|
| 4 | F | F | H | ![triazolone with H5C2, F3C, =O] | 110 |
| 5 | F | —NH—SO$_2$—C$_2$H$_5$ | H | ![triazolone with H5C2, F3C, =O] | 143 |
| 6 | F | —O—CH(CH$_3$)—C≡CH | H | ![triazolethione with H3C, F2CH, =S] | 162 |

TABLE 1-continued

Examples of the compounds of the formula (I)

| Ex. No. | R[1] | R[2] | R[3] | Z | Melting point (° C.) |
|---|---|---|---|---|---|
| 7 | F | —NH—SO$_2$—C$_2$H$_5$ | H | 4-(methylamino)-3-methyl-1H-1,2,4-triazol-5(4H)-one (H$_3$C—NH on N4, H$_3$C at C3, =O at C5, N1-linked) | 237 (Triethylammonium salt) |
| 8 | F | F | H | 4-methyl-3-(difluoromethyl)-1H-1,2,4-triazole-5(4H)-thione (H$_3$C on N4, F$_2$CH at C3, =S at C5) | 220 |
| 9 | F | —NH—SO$_2$—C$_2$H$_5$ | H | 4-methyl-3-(difluoromethyl)-1H-1,2,4-triazol-5(4H)-one (H$_3$C on N4, F$_2$CH at C3, =O at C5) | 218 |
| 10 | F | —NH—SO$_2$—C$_2$H$_5$ | H | 5-(dimethylamino)-1-methyl-3-(trifluoromethyl)-1H-1,2,4-triazole (N(CH$_3$)$_2$ at C5, F$_3$C at C3) | 185 |
| 11 | F | F | H | 3-methyl-6,7,8,8a-tetrahydro-[1,2,4]triazolo[4,3-a]pyridin-3(2H)-one (fused cyclohexane-triazolone, =O) | 218 |
| 12 | F | —OC$_2$H$_5$ | H | 3-methyl-6,7,8,8a-tetrahydro-[1,2,4]triazolo[4,3-a]pyridin-3(2H)-one | 202 |
| 13 | F | —NH—SO$_2$—C$_2$H$_5$ | H | 4-methyl-3-cyclopropyl-1H-1,2,4-triazol-5(4H)-one (H$_3$C on N4, cyclopropyl at C3, =O at C5) | 210 |
| 14 | F | —NH—SO$_2$—C$_2$H$_5$ | H | 4-ethyl-3-(difluoromethyl)-1H-1,2,4-triazol-5(4H)-one (H$_5$C$_2$ on N4, F$_2$CH at C3, =O at C5) | 203 |
| 15 | F | F | H | 4-methyl-3-(difluoromethyl)-1H-1,2,4-triazol-5(4H)-one (H$_3$C on N4, F$_2$CH at C3, =O at C5) | 185 |

TABLE 1-continued

Examples of the compounds of the formula (I)

| Ex. No. | R¹ | R² | R³ | Z | Melting point (° C.) |
|---|---|---|---|---|---|
| 16 | F | —N(CH₃)—SO₂—C₂H₅ | H | 4-ethyl-3-(trifluoromethyl)-1-methyl-1,2,4-triazol-5(4H)-one | 170 |
| 17 | F | —OCH(CH₃)₂ | H | 2-methyl-6,7,8,8a-tetrahydro-[1,2,4]triazolo[4,3-a]pyridin-3(2H)-one | 206 |
| 18 | F | OH | H | 2-methyl-6,7,8,8a-tetrahydro-[1,2,4]triazolo[4,3-a]pyridin-3(2H)-one | 250 |
| 19 | F | —N(CH₃)—SO₂—C₂H₅ | H | 6-(trifluoromethyl)-1,3-dimethylpyrimidine-2,4(1H,3H)-dione | 98 |
| 20 | F | —NH—SO₂—C₂H₅ | H | 6-(trifluoromethyl)-1,3-dimethylpyrimidine-2,4(1H,3H)-dione | 208 |
| 21 | F | —NH—SO₂—C₂H₅ | H | 6-(trifluoromethyl)-1,3-dimethyl-2-thioxo-pyrimidin-4(1H,3H)-one | 55 |
| 22 | F | —NH—SO₂—C₂H₅ | H | 3,4-dimethyl-1-methyl-1H-pyrrole-2,5-dione | (amorphous) |
| 23 | F | —NH—SO₂—C₂H₅ | H | 2-methyl-4,5,6,7-tetrahydro-1H-isoindole-1,3(2H)-dione | 183 |

TABLE 1-continued
Examples of the compounds of the formula (I)
| Ex. No. | R¹ | R² | R³ | Z | Melting point (° C.) |
|---|---|---|---|---|---|
| 24 | F | —N(CH₃)—SO₂—CH₃ | H | 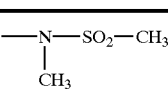 | 167 |
| 25 | F | —NH—SO₂—CH₃ | H | 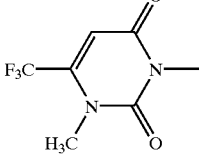 | 130 |
| 26 | F | —NH—SO₂—CH₃ | H | 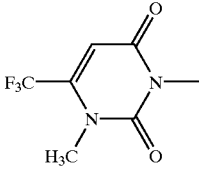 | 243 |
| 27 | F | F | H | 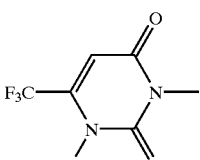 | 199 |
| 28 | F | —NH—SO₂—C₂H₅ | H | 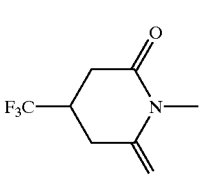 | 202 |
| 29 | F | —NH—SO₂—CH₃ | H | 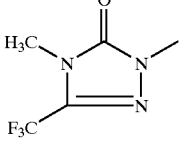 | 200 |
| 30 | F | —NH—SO₂—CH(CH₃)₂ | H | 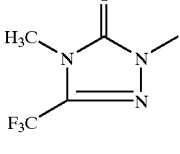 | 204 |
| 31 | F | —NH—SO₂—C₂H₅ | H | 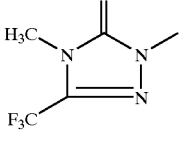 | 195 |

TABLE 1-continued

Examples of the compounds of the formula (I)

| Ex. No. | R$^1$ | R$^2$ | R$^3$ | Z | Melting point (° C.) |
|---|---|---|---|---|---|
| 32 | F | —O—CH(CH$_3$)—C≡CH | H | 1,4-dimethyl-3-trifluoromethyl-1,2,4-triazol-5(4H)-one | 122 |
| 33 | F | —O—CH$_2$—C≡CH | H | 1,4-dimethyl-3-trifluoromethyl-1,2,4-triazol-5(4H)-one | 190 |
| 34 | F | —NH—SO$_2$—CH$_3$ | H | 1,4-dimethyl-3-trifluoromethyl-1,2,4-triazole-5(4H)-thione | 178 |
| 35 | F | —NH—SO$_2$—C$_3$H$_7$ | H | 1,4-dimethyl-3-trifluoromethyl-1,2,4-triazol-5(4H)-one | 203 |
| 36 | F | —NH—SO$_2$—C$_2$H$_5$ | H | 4-isopropyl-1-methyl-3-propyl-1,2,4-triazol-5(4H)-one | 199 |
| 37 | F | —NH—SO$_2$—C$_2$H$_5$ | H | 3-butyl-4-ethyl-1-methyl-1,2,4-triazol-5(4H)-one | 153 |
| 38 | F | —NH—SO$_2$—C$_2$H$_5$ | H | 3-isopropyl-4-isopropyl-1-methyl-1,2,4-triazol-5(4H)-one | 206 |
| 39 | F | —NH—SO$_2$—C$_2$H$_5$ | H | 3-cyclopropyl-1-methyl-4-propyl-1,2,4-triazol-5(4H)-one | 167 |

TABLE 1-continued
Examples of the compounds of the formula (I)
| Ex. No. | R¹ | R² | R³ | Z | Melting point (° C.) |
|---|---|---|---|---|---|
| 40 | F | F | H | 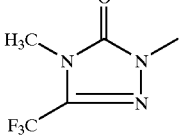 | 130 |
| 41 | F | —OCH₂CF₃ | H | 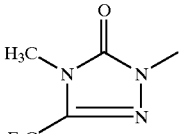 | 173 |
| 42 | F | —OC₂H₄OCH₃ | H | 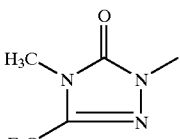 | 148 |
| 43 | F | —OC₂H₅ | H | 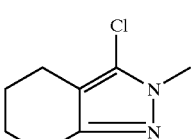 | 155 |
| 44 | F | —OC₃H₇ | H | 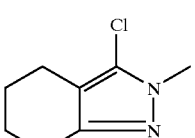 | 130 |
| 45 | F | F | H | 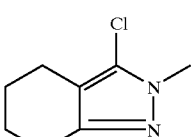 | 131 |
| 46 | F | —OCH(CH₃)₂ | H | 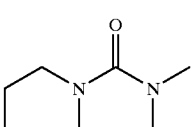 | 202 |
| 47 | F | —OC₂H₅ | H | 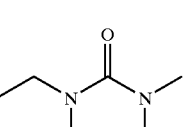 | 185 |
| 48 | F | —NH—SO₂—C₂H₅ | H | 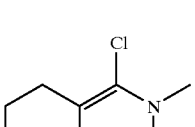 | 111 |

TABLE 1-continued

Examples of the compounds of the formula (I)

| Ex. No. | R¹ | R² | R³ | Z | Melting point (° C.) |
|---|---|---|---|---|---|
| 49 | H | —NH—SO₂—C₂H₅ | H | 4-chloro-2-methyl-4,5,6,7-tetrahydro-2H-indazole | 118 |
| 50 | F | —NH—SO₂—C₃H₇-n | H | 4-chloro-2-methyl-4,5,6,7-tetrahydro-2H-indazole | 143 |
| 51 | F | —OC₂H₄OC₂H₄OCH₃ | H | 4-(difluoromethyl)-2-methyl-5-methyl-1,2,4-triazol-3(4H)-one | 168 |
| 52 | F | —NH—SO₂—C₃H₇-n | H | 1,3-dimethyl-6-trifluoromethyl-2-thioxo-pyrimidin-4(3H)-one | (amorphous) |
| 53 | F | —NH—SO₂—C₃H₇-n | H | 1,3-dimethyl-6-trifluoromethyl-pyrimidine-2,4(1H,3H)-dione | 232 |
| 54 | F | —NH—SO₂—C₃H₇-i | H | 1,3-dimethyl-6-trifluoromethyl-pyrimidine-2,4(1H,3H)-dione | 226 |
| 55 | F | —NH—SO₂—C₃H₇-i | H | 4-ethyl-2-methyl-5-trifluoromethyl-1,2,4-triazol-3(4H)-one | 187 |
| 56 | F | —NH—SO₂C₃H₇-i | H | 2-methyl-5,6,7,8-tetrahydro-[1,2,4]triazolo[4,3-a]pyridin-3(2H)-one | 236 |

TABLE 1-continued

Examples of the compounds of the formula (I)

| Ex. No. | R¹ | R² | R³ | Z | Melting point (° C.) |
|---|---|---|---|---|---|
| 57 | F | —NH—SO₂C₃H₇-i | H | (7-membered ring fused triazolone, N-methyl) | 252 |
| 58 | F | —NH—SO₂C₃H₇-i | H | 4-methyl-3-(difluoromethyl)-1-methyl-triazol-5(4H)-one | 109 |
| 59 | F | —NH—SO₂C₃H₇-i | H | 4-ethyl-3-(difluoromethyl)-1-methyl-triazol-5(4H)-one | 207 |
| 60 | F | —NH—SO₂C₃H₇-i | H | 6,6-dimethyl-fused triazolone, N-methyl | 215 |
| 61 | F | —N(CH₃)—SO₂C₂H₅ | H | 4-methyl-3-(trifluoromethyl)-1-methyl-triazol-5(4H)-one | 102 |
| 62 | F | —NH—SO₂—C₂H₅ | H | 4-methyl-3-methyl-1-methyl-triazol-5(4H)-one | 185 |
| 63 | Cl | —NH—SO₂—C₂H₅ | H | 4-methyl-3-(trifluoromethyl)-1-methyl-triazol-5(4H)-one | 121 |
| 64 | F | F | H | 4-(difluoromethyl)-3-methyl-1-methyl-triazol-5(4H)-one | 157 |
| 65 | F | —NH—SO₂—C₂H₅ | H | bicyclic hexahydro imidazo-pyridine dione, N-methyl | 195 |

TABLE 1-continued

Examples of the compounds of the formula (I)

| Ex. No. | R¹ | R² | R³ | Z | Melting point (° C.) |
|---|---|---|---|---|---|
| 66 | F | —OH | H | 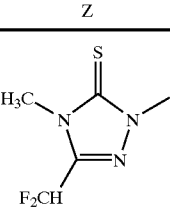 | 193 (decomp) DBU salt |

Preparation of the Starting Compounds

EXAMPLE II-1

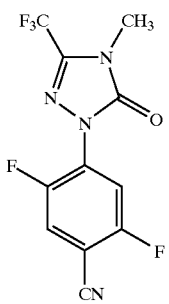

5.8 g (0.042 mol) of potassium carbonate are added at room temperature to 6.3 g (0.034 mol) of 4-methyl-3-trifluoromethyl-1,2,4-triazolin-5-one (cf. e.g. U.S. Pat. No. 3,780,052) and 5.4 g (0.034 mol) of 2,4,5-trifluorobenzonitrile (cf. e.g. EP 191181) in 150 ml of dimethyl sulphoxide and the mixture is subsequently heated at 100° C. for 14 hours. For working up, the cooled reaction mixture is placed in water, adjusted to a pH of 2 with dilute hydrochloric acid and subjected several times to extraction with dichloromethane. The combined organic phases are dried over sodium sulphate and concentrated in vacuo. The residue is chromatographed over silica gel (eluent: dichloromethane).

6.2 g (60% of theory) of 1-(4-cyano-2,5-difluorophenyl)-4-methyl-3-trifluoromethyl-1,2,4-triazolin-5-one are obtained of melting point 74° C.

EXAMPLE II-2

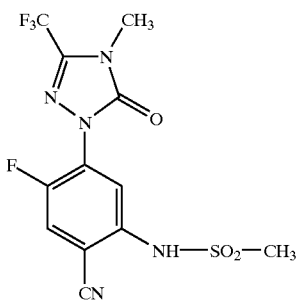

0.83 g (0.006 mol) of potassium carbonate is added at room temperature to 1.52 g (0.005 mol) of 1-(4-cyano-2,5-difluorophenyl)4-methyl-3-trifluoromethyl-1,2,4-triazolin-5-one and 0.48 g (0.005 mol) of methanesulphonamide in 50 ml of dimethyl sulphoxide and the mixture is subsequently heated at 120° C. for 12 hours. For working up, the cooled reaction mixture is placed in water, adjusted to a pH of 2 with dilute hydrochloric acid and subjected several times to extraction with dichloromethane. The combined organic phases are dried over sodium sulphate and concentrated in vacuo. The residue is chromatographed over silica gel (eluent: dichloromethane/methanol 20:1).

0.55 g (28% of theory) of 1-(4-cyano-2-fluoro-5-methylsulphonylaminophenyl)4-methyl-3-trifluoromethyl-1,2,4-triazolin-5-one is obtained of melting point 67° C.

EXAMPLE II-3

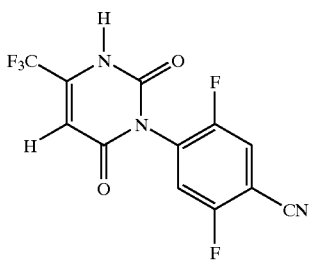

0.3 g (10 mmol) of sodium hydride (80%) is added at from 0° C. to 5° C. to an initial charge of 1.8 g (10 mmol) of ethyl 3-amino-4,4,4-trifluoro-crotonate in 30 ml of dimethylformamide and 2 ml of toluene. The mixture is stirred at from 0° C. to 5° C. for 30 minutes. After the mixture has been cooled to −70° C., 0.9 g (5 mmol) of 4-cyano 2,5-difluorophenyl isocyanate—dissolved in 10 ml of toluene—is added and the mixture is stirred at from −60° C. to −70° C. for 150 minutes. After the cooling bath has been removed, 2 ml of acetic acid are added. The mixture is then diluted with water to about twice the volume and subjected to extraction with ethyl acetate. The organic phase is concentrated and the residue is crystallized with diisopropyl ether.

1.1 g (69% of theory) of 1-(4-cyano-2,5-difluoro-phenyl)-3,6dihydro-2,6-dioxo-4-trifluoromethyl-1-(2H)-pyrimidine are obtained of melting point 194° C.

EXAMPLE II-4

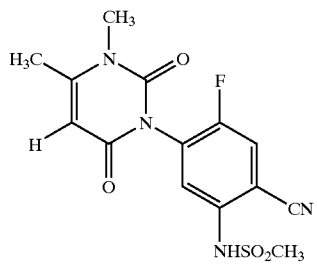

A mixture of 0.83 g (3 mmol) of 1-(4-cyano-2,5-difluorophenyl)-3,6-dihydro-2,6-dioxo 3,4-dimethyl-1(2H)-pyrimidine, 0.32 g (3 mmol) of methane sulphonamide, 0.6 g of potassium carbonate and 10 m of dimethyl sulphoxide is heated at 120° C. for 10 hours. After cooling, the mixture is poured into ice-water and acidfied with 2 N hydrochloric acid. It is then subjected to extraction with ethyl acetate and organic phase is washed with water, dried with sodium sulphate and filtered. The solvent is carefully removed from the filtrate by distillation under a water-pump vacuum.

0.8 g (76% of theory) of 1-(4-cyano-2-fluoro-5-methylsulphonylaminophenyl)-3,6-dihydro-2,6-dioxo-3,4-dimethyl-1(2H)-pyrimidine is obtained as crystalline residue (melting point >250° C.).

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

TABLE A

Pre-emergence test/greenhouse

| Active compound (Synthesis Example Number) | Application rate (g/ha) | Barley | Maize | Amaranthus | Chenopodium | Matricaria | Portulaca | Solanum |
|---|---|---|---|---|---|---|---|---|
| (3) | 125 | 0 | 0 | 100 | 100 | 100 | 100 | 100 |
| (5) | 125 | 0 | 0 | 100 | 100 | 90 | 90 | 100 |
| (6) | 125 | 0 | 30 | 100 | 100 | 95 | 100 | 100 |
| (7) | 125 | 30 | 0 | 100 | 100 | 95 | 100 | 95 |

TABLE B

Pre-emergence test/greenhouse

| Active compound (Synthesis Example Number) | Application rate (g/ha) | Wheat | Maize | Abuthilon | Amaranthus | Chenopodium | Matricaria | Portulaca | Solanum |
|---|---|---|---|---|---|---|---|---|---|
| 19 | 60 | 10 | 0 | 100 | 95 | 100 | 100 | 100 | 100 |
| 20 | 60 | 20 | 0 | 100 | 100 | 100 | 100 | 100 | 100 |
| 21 | 60 | 0 | 0 | 100 | 100 | 100 | 100 | 100 | 100 |
| 22 | 250 | 0 | 20 | 100 | 100 | 100 | 100 | 95 | 100 |
| 23 | 60 | 0 | 0 | 95 | 70 | 95 | 100 | 95 | 70 |
| 24 | 30 | 0 | 20 | 100 | 95 | 100 | 100 | 100 | 100 |
| 25 | 30 | 0 | 0 | 100 | 100 | 90 | 100 | 100 | 100 |
| 26 | 60 | 0 | 0 | 100 | 80 | 100 | 100 | 100 | 90 |
| 4 | 250 | 0 | 10 | 80 | 50 | 70 | 95 | 90 | 70 |
| 5 | 125 | 0 | 0 | 10 | 100 | 100 | 70 | 90 | 100 |
| 3 | 60 | 0 | 0 | 100 | 100 | 100 | 100 | 100 | 100 |
| 6 | 60 | 20 | 30 | 100 | 100 | 100 | 100 | 100 | 95 |
| 7 | 125 | 50 | 0 | 95 | 100 | 100 | 95 | 100 | 95 |
| 8 | 60 | 40 | 0 | 100 | 100 | 100 | 95 | 95 | 100 |
| 9 | 60 | 0 | 0 | 100 | 100 | 100 | 95 | 90 | 100 |
| 1 | 125 | 0 | 0 | 100 | 100 | 100 | 95 | 100 | 100 |
| 12 | 60 | 20 | 0 | 70 | 70 | 100 | 95 | 95 | 70 |

TABLE B-continued

Pre-emergence test/greenhouse

| Active compound (Synthesis Example Number) | Application rate (g/ha) | Wheat | Maize | Abu-thilon | Amaran-thus | Cheno-podium | Matri-caria | Portu-laca | Sola-num |
|---|---|---|---|---|---|---|---|---|---|
| 13 | 60 | 0 | 0 | 100 | 100 | 100 | 70 | 90 | 100 |
| 16 | 60 | 10 | 0 | 95 | 20 | 100 | 90 | 80 | 80 |
| 17 | 30 | 0 | 0 | 100 | 100 | 100 | 100 | 100 | 100 |
| 28 | 60 | 0 | 20 | 100 | 100 | 100 | 100 | 100 | 100 |
| 29 | 60 | 0 | 0 | 100 | 100 | 100 | 100 | 100 | 100 |
| 30 | 60 | 0 | 0 | 100 | 100 | 100 | 90 | 100 | 100 |
| 31 | 60 | 0 | 0 | 100 | 100 | 100 | 100 | 100 | 100 |
| 32 | 30 | 10 | 0 | — | 100 | 100 | 100 | 95 | 100 |
| 33 | 30 | 10 | 10 | 95 | 95 | 100 | 100 | 100 | 100 |
| 34 | 60 | 0 | 0 | 100 | 100 | 100 | 100 | 100 | 100 |
| 35 | 60 | 0 | 0 | 100 | 100 | 100 | 90 | 95 | 100 |
| 40 | 250 | 20 | 0 | 30 | 40 | 100 | 95 | 100 | 80 |
| 41 | 60 | 20 | 30 | 100 | 100 | 100 | 100 | 100 | 100 |
| 45 | 125 | 0 | 0 | 95 | 100 | 100 | 100 | 90 | 95 |
| 46 | 60 | 0 | 70 | 100 | 100 | 100 | 100 | 100 | 100 |
| 47 | 30 | 0 | 0 | 100 | 95 | 100 | 100 | 100 | 100 |
| 48 | 60 | 0 | 0 | 100 | 100 | 100 | 100 | 100 | 100 |
| 51 | 30 | 0 | 20 | 100 | — | 100 | 95 | 100 | 100 |

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. After three weeks, the degree of damage to the plants is rated in % damage in comparison to the development of the untreated control.

The figures denote:

0%=no action (like untreated control)

100%=total destruction

TABLE C

Post-emergence test/greenhouse

| Active compound (Synthesis Example Number) | Application rate (g/ha) | Wheat | Maize | Abu-thilon | Amaran-thus | Cheno-podium | Sola-num | Vero-nica |
|---|---|---|---|---|---|---|---|---|
| 19 | 4 | 5 | 20 | 95 | 95 | 95 | 100 | 100 |
| 20 | 4 | 0 | 15 | 100 | 95 | 95 | 100 | 95 |
| 21 | 4 | 5 | 60 | 90 | 100 | 70 | 100 | 100 |
| 22 | 30 | 15 | 0 | 100 | 100 | 40 | 100 | 20 |
| 23 | 30 | 0 | 50 | 95 | — | 90 | 100 | 100 |
| 24 | 30 | 15 | 70 | 100 | 100 | 100 | 100 | 100 |
| 25 | 15 | 0 | 50 | 100 | 100 | 100 | 100 | 100 |
| 26 | 15 | 0 | 30 | 50 | 90 | 50 | 50 | 100 |
| 5 | 15 | 10 | 20 | 100 | 100 | 100 | 100 | 100 |
| 3 | 30 | 10 | 30 | 100 | 100 | 100 | 100 | 100 |
| 6 | 8 | 30 | 50 | 100 | 100 | 100 | 100 | 95 |
| 7 | 60 | 10 | 50 | 100 | 100 | 95 | 100 | 95 |
| 8 | 60 | 10 | 30 | 100 | 100 | 100 | 100 | 100 |
| 9 | 60 | 10 | 30 | 100 | 100 | 100 | 100 | 100 |
| 1 | 15 | 10 | 50 | 100 | 95 | 95 | 100 | 100 |
| 12 | 8 | 10 | 30 | 100 | 100 | 95 | 100 | 100 |
| 13 | 15 | 0 | 30 | 95 | 100 | 80 | 100 | 90 |
| 16 | 60 | 20 | 60 | 95 | 100 | 100 | 100 | 100 |
| 17 | 8 | 10 | 10 | 100 | 100 | 95 | 100 | 100 |
| 28 | 30 | 0 | 30 | 100 | 100 | 90 | 100 | 100 |
| 29 | 8 | 5 | 0 | 70 | 100 | 90 | 100 | 95 |
| 30 | 8 | 0 | 50 | 100 | 100 | 95 | 100 | 70 |
| 31 | 8 | 0 | 70 | 100 | 100 | 90 | 100 | 100 |
| 32 | 4 | 15 | 30 | 100 | 100 | 95 | 100 | 100 |
| 33 | 4 | 20 | 60 | 100 | 100 | 100 | 100 | 100 |
| 34 | 15 | 0 | 30 | 100 | 100 | 100 | 100 | 100 |

TABLE C-continued

Post-emergence test/greenhouse

| Active compound (Synthesis Example Number) | Application rate (g/ha) | Wheat | Maize | Abu-thilon | Amaran-thus | Cheno-podium | Sola-num | Vero-nica |
|---|---|---|---|---|---|---|---|---|
| 35 | 30 | 0 | 25 | 100 | 100 | 90 | 100 | 95 |
| 40 | 125 | 10 | 5 | 50 | 70 | 100 | 100 | 90 |
| 41 | 15 | 20 | 50 | 100 | 80 | 90 | 100 | 95 |
| 43 | 15 | 0 | 50 | 100 | 95 | 100 | 100 | 100 |
| 44 | 8 | 0 | 15 | 100 | 100 | 100 | 95 | 100 |
| 45 | 8 | 10 | 40 | 95 | 95 | 95 | 100 | — |
| 46 | 8 | 15 | 20 | 100 | 100 | 95 | 100 | 100 |
| 47 | 8 | 10 | 10 | 100 | 100 | 95 | 100 | 100 |
| 48 | 8 | 5 | 60 | 100 | 100 | 80 | 100 | 100 |
| 49 | 8 | 0 | 60 | 60 | 100 | 10 | 100 | 100 |
| 50 | 15 | 5 | 70 | 100 | 95 | 80 | 100 | 95 |
| 51 | 15 | 15 | 60 | 100 | 100 | 70 | 100 | 100 |

What is claimed is:

1. A substituted aromatic thiocarboxamide compound of the formula:

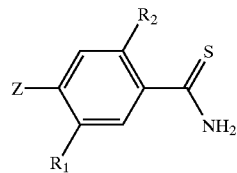

wherein, $R^1$ is chlorine or fluorine;

$R_2$ is $NHSO_2CH_3$, $NHSO_2CH(CH_3)_2$, or $NHSO_2C_2H_5$; and

Z is

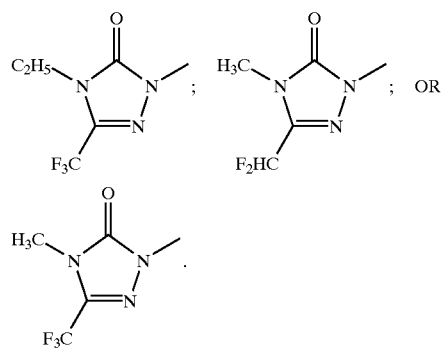

2. The compound of claim 1, wherein
$R^1$ is fluorine;
$R_2$ is $NHSO_2C_2H_5$; and
Z is

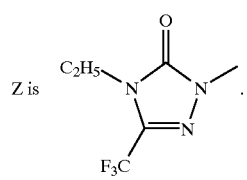

3. The compound of claim 1, wherein
$R^1$ is fluorine;
$R_2$ is $NHSO_2C_2H_5$; and

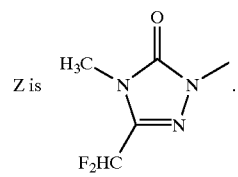

4. The compound of claim 1, wherein
$R^1$ is fluorine;
$R^2$ is $NHSO_2C_2H_5$; and Z is

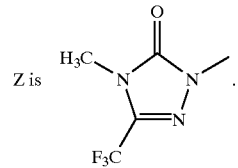

5. The compound of claim 1, wherein
$R^1$ is fluorine;
$R_2$ is $NHSO_2CH_3$; and Z is

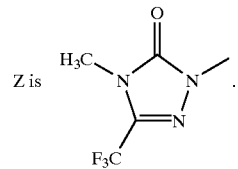

6. The compound of claim 1, wherein
$R^1$ is fluorine;

$R_2$ is $NHSO_2CH(CH_3)_2$; and

Z is 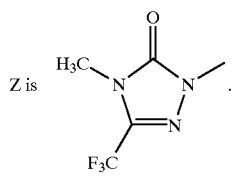

7. The compound of claim 1, wherein
$R^1$ is chlorine;
$R_2$ is $NHSO_2C_2H_5$; and Z is 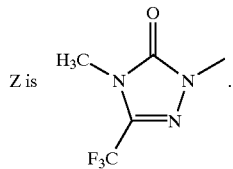

8. An herbicidal composition comprising at least one substituted aromatic thiocarboxamide compound of any one of claims 1–7 and an extender.

9. A method of combatting unwanted plants comprising applying an herbicially effective amount of a substituted aromatic thiocarboxamide compound of any one of claims 1–7 to said unwanted plants or to an area in which it is desired to exclude said unwanted plants.

10. A process for the preparation of the substituted aromatic thiocarboxamide compound of claim 1, wherein substituted aromatic nitriles of the formula:

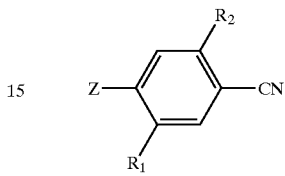

in which $R^1$, $R_2$ and Z are as defined in claim 1, are reacted with hydrogen sulfide or with thioacetamide, optionally in the presence of a reaction auxiliary and optionally in the presence of a diluent.

* * * * *

UNITED STATES PATENT AND TRADEMARK OFFICE
CERTIFICATE OF CORRECTION

PATENT NO. : 6,420,316 B1
DATED : July 16, 2002
INVENTOR(S) : Karl-Heinz Linker

It is certified that error appears in the above-identified patent and that said Letters Patent is hereby corrected as shown below:

<u>Title page,</u>
Item [56], References Cited, after 5,124,342 change "6/1992" to -- 5/1985 --
OTHER PUBLICATIONS, change "2-arly" to -- 2-aryl --

Signed and Sealed this

Eighteenth Day of March, 2003

JAMES E. ROGAN
*Director of the United States Patent and Trademark Office*